(12) United States Patent
Hirose et al.

(10) Patent No.: US 9,708,594 B2
(45) Date of Patent: Jul. 18, 2017

(54) THERMOSTABLE β-GLUCOSIDASE

(71) Applicant: HONDA MOTOR CO., LTD., Minato-Ku, Tokyo (JP)

(72) Inventors: Yoshitsugu Hirose, Wako (JP); Takahiro Gunji, Wako (JP); Asuka Yamaguchi, Wako (JP); Migiwa Suda, Wako (JP); Jiro Okuma, Wako (JP); Yasuhiro Kondo, Wako (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/850,407

(22) Filed: Sep. 10, 2015

(65) Prior Publication Data
US 2016/0076015 A1    Mar. 17, 2016

(30) Foreign Application Priority Data

Sep. 11, 2014 (JP) ................................. 2014-184910

(51) Int. Cl.
| C12N 9/26 | (2006.01) |
| C12P 19/14 | (2006.01) |
| C12N 9/42 | (2006.01) |
| C12P 19/02 | (2006.01) |

(52) U.S. Cl.
CPC ......... *C12N 9/2445* (2013.01); *C12N 9/2434* (2013.01); *C12P 19/02* (2013.01); *C12P 19/14* (2013.01); *C12Y 302/01021* (2013.01)

(58) Field of Classification Search
None
See application file for complete search history.

(56) References Cited

U.S. PATENT DOCUMENTS 9,512,414 B2 * 12/2016 Okuma ................... C12P 19/02

FOREIGN PATENT DOCUMENTS

| JP | 10-052274 A | 2/1998 |
| JP | 4689807 B | 5/2011 |
| JP | 4801872 B | 10/2011 |
| WO | 2009146464 A2 | 12/2009 |
| WO | 2010006152 A2 | 1/2010 |

OTHER PUBLICATIONS

GenBank Database Accession No. JF508852, Jun. 2012, 2 pages.*
UniProt Accession No. B9K7M5, May 2013, 2 pages.*
Parry et al., "Biochemical characterization and mechanism of action of a thermostable Beta-glucosidase purified from Thermoascus aurantiacus", Biochemical Journal, 2001, vol. 353, p. 117-127.
Jabbour et al., "A novel thermostable and glucose-tolerant Beta-glucosidase from Fervidobacterium islandicum" Applied Microbiology and Biotechnology, 2012, vol. 93, p. 1947-1956.
Quinlan et al., "Pyrobayes: an improved base caller for SNP discovery in pyrosequences" Nature Methods, 2008, vol. 5, p. 179-181.
Hoff et al. "Orphelia: predicting genes in metagenomic sequencing reads", Nucleic Acids Research, 2009, 37, Web Server issue : W101-W105.
Finn et al., "The Pfam protein families database", Nucleic Acids Research Database, 2010, vol. 38, Database issue p. D211-D222.
Durbin et al., 'The Theory Behind Profile HMMs. Biological sequence analysis: Biological sequence analysis: probabilistic models of proteins and nucleic acids', 1998, Cambridge University Press.
Office Action Search Report mailed Nov. 26, 2015 corresponding to Patent Application No. EP15184665.6.
Yernool et al., "Cloning and Characterization of the Glucooligosaccharide Catabolic Pathway Beta-Glucan Glucohydrolase and Cellobiose Phosphorylase in the Marine Hyperthermophile Thermotoga neapolitana," Journal of Bacteriology, Sep. 2000, pp. 5172-5179, vol. 182, No. 18, American Society for Microbiology.
Gao et al., "Purification and Characterization of a New Beta-Glucosidase from Penicillium piceum and its Application in Enzymatic Degradation of Delignified Corn Stover," Bioresource Technology, 2013, pp. 658-661, vol./Issue 147, Elsevier Ltd.
Dotsenko et al., "Characterization of a GH Family 3 Beta-Glycoside Hydrolase from Chrysosporium lucknowense and its Application to the Hydrolysis of Beta-Glucan and Xylan," Bioresource Technology, 2012, pp. 345-349, vol./Issue 112, Elsevier Ltd.
Schroder et al., "Characterization of a Heat-Active Archaeal Beta-Glucosidase From a Hydrothermal Spring Metagenome," Enzyme and Microbial Technology, 2014, pp. 48-54, vol./Issue 57, Elsevier Ltd.
Zhou et al., "Beta-Xylosidase Activity of a GH3 Glucosidase/Xylosidase From Yak Rumen Metagenome Promotes the Enzymatic Degradation of Hemicellulosic Xylans," Letters in Applied Microbiology, 2011, pp. 79-87, vol./Issue 54, The Society for Applied Microbiology.

* cited by examiner

*Primary Examiner* — David J Steadman
(74) *Attorney, Agent, or Firm* — Carrier Blackman & Associates, P.C.; William D. Blackan; Fulchand P. Shende

(57) ABSTRACT

An isolated recombinant thermostable β-glucosidase includes a polypeptide including the amino acid sequence of SEQ ID NO: 1 and at least one region selected from the group consisting of a cellulose-binding module, linker domain, a signal peptide and a tag.

5 Claims, 5 Drawing Sheets

FIG. 1

THERMOSTABLE β-GLUCOSIDASE

TECHNICAL FIELD

The present invention relates to a thermostable β-glucosidase, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Priority is claimed on Japanese Patent Application No. 2014-184910, filed Sep. 11, 2014, the content of which is incorporated herein by reference.

BACKGROUND ART

Plant biomass or lignocellulose is the most abundant renewable energy source on earth. From the viewpoints of global environmental conservation and fossil fuel depletion, the biorefinery using plant biomass as a biofuel or a raw material of chemical products such as ethanol has attracted attention. The main component in the dry weight of plant biomass is lignocellulose composed of polysaccharides, such as celluloses and hemicelluloses, and lignin. For example, polysaccharides are hydrolyzed into monosaccharides such as glucose and xylose by glycoside hydrolases, and are then used as a biofuel or a raw material of chemical products.

Lignocellulose having a complex structure is persistent and is difficult to degrade or hydrolyze with a single glycoside hydrolase enzyme. For the complete degradation of lignocellulose, in general, three types of enzymes, i.e., an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21) are required. In addition, it is considered that an appropriate formulation of multiple enzymes is necessary, including a xylanase (endo-1,4-β-xylanase, EC 3.2.1.8) which is a hemicellulase and other plant cell wall degrading enzymes.

When cellulose is subjected to hydrolysis by cellobiohydrolase, cellobiose which is a disaccharide is mainly produced. β-glucosidase hydrolyzes this cellobiose into glucose, which is a monosaccharide, and is therefore one of the essential enzymes for degrading lignocellulose ultimately to monosaccharides.

In the conventional lignocellulose to ethanol conversion process, high-solid loading up to 30-60% in initial substrate concentration has been attempted for the purpose of higher energy efficiency and less water usage. The enzymatic hydrolysis of lignocellulose by such high-solid loading processes results in the high viscosity of the hydrolyzed biomass solution so that the hydrolysis of lignocellulose hardly proceeds. Therefore, for example, by carrying out the enzymatic hydrolysis process at a high temperature of 80° C. or higher using a thermostable enzyme, in addition to an increase in the hydrolysis reaction rate, since the viscosity of the saccharified biomass solution also reduces, the shortening of the hydrolysis reaction time and the reduction of the amount of enzyme are expected to be achieved. For this reason, for various glycoside hydrolases, development of enzymes that are more excellent in terms of thermostability has been desired.

Many thermostable enzymes have been obtained by cloning the genes from the thermophilic microorganisms that live in a high temperature environment and determining the DNA sequence thereof, followed by the expression thereof using *Escherichia coli*, filamentous fungi and the like. For example, a thermostable β-glucosidase (with an optimum temperature of 70° C. and an optimum pH of 3.5 to 4.0) derived from a filamentous fungus *Acremonium cellulolyticus* has been disclosed in Patent Document 1. Three types of thermostable β-glucosidases (with an optimum temperature of 55° C. and an optimum pH of 4.5 to 5.1) derived from *Acremonium cellulolyticus* have been disclosed in Patent Document 2. A thermostable β-glucosidase (with an optimum temperature of 80° C. and an optimum pH of 5 to 6) derived from a *Thermoanaerobactor* species has been disclosed in Patent Document 3. A thermostable β-glucosidase (with an optimum temperature of 80° C. and an optimum pH of 4.6) derived from *Thermoascas auranticus* has been disclosed in Non-Patent Document 1. A thermostable β-glucosidase (with an optimum temperature of 90° C. and an optimum pH of 6 to 7) derived from *Fervidobacterium islandicum* has been disclosed in Non-Patent Document 2.

PRIOR ART DOCUMENTS

Patent Documents

[Patent Document 1] Japanese Patent No. 4801872
[Patent Document 2] Japanese Patent No. 4689807
[Patent Document 3] Japanese Unexamined Patent Application, First Publication No. Hei 10-52274

Non-Patent Documents

[Non-Patent Document 1] Neil et al., Biochemical Journal, 2001, vol. 353, p. 117-127.
[Non-Patent Document 2] Jabbour et al., Applied Microbiology and Biotechnology, 2012, vol. 93, p. 1947-1956.

SUMMARY OF THE INVENTION

Problems to be Solved by the Invention

It is an object of the present invention to provide a novel thermostable β-glucosidase which exhibits hydrolytic activity using p-nitrophenyl-β-D-glucopyranoside (hereinafter, may be abbreviated as PNPG) as a substrate at least under conditions of a temperature of 85° C. and a pH of 7.5, a polynucleotide that encodes the aforementioned thermostable β-glucosidase, an expression vector for expressing the aforementioned thermostable β-glucosidase, a transformant incorporated with the aforementioned expression vector, and a method for producing a cellulose degradation product using the aforementioned thermostable β-glucosidase.

Means for Solving the Problem

In order to solve the above-mentioned problems, the inventors of the present invention have successfully obtained thermostable β-glucosidases having novel amino acid sequences by extracting DNA directly from hot spring high temperature soils and conducting large-scale metagenome sequencing of hardly culturable microbiota. This has led to the completion of the present invention.

That is, as the thermostable β-glucosidase, polynucleotide, expression vector, transformant, method for producing a thermostable β-glucosidase, glycoside hydrolase mixture and method for producing a cellulose degradation product according to the present invention, the following aspects [1] to [10] can be mentioned.

[1] A thermostable β-glucosidase including a β-glucosidase catalytic domain, the β-glucosidase catalytic domain including: (A) a polypeptide including an amino acid sequence represented by SEQ ID NO: 1;
(B) a polypeptide including an amino acid sequence in which at least one amino acid is deleted, substituted, or added in the amino acid sequence represented by SEQ ID NO: 1, and having hydrolytic activity using p-nitrophenyl-β-D-glucopyranoside as a substrate at least under conditions of a temperature of 85° C. and a pH of 7.5; or
(C) a polypeptide including an amino acid sequence having at least 60% sequence identity with the amino acid sequence represented by SEQ ID NO: 1, and having hydrolytic activity using p-nitrophenyl-β-D-glucopyranoside as a substrate at least under conditions of a temperature of 85° C. and a pH of 7.5.

[2] The thermostable β-glucosidase according to the aforementioned aspect [1], which also has xylanase activity.

[3] A polynucleotide including a region that encodes a β-glucosidase catalytic domain which includes: (a) a nucleotide sequence that encodes a polypeptide including an amino acid sequence represented by SEQ ID NO: 1;
(b) a nucleotide sequence that encodes a polypeptide including an amino acid sequence in which at least one amino acid is deleted, substituted, or added in the amino acid sequence represented by SEQ ID NO: 1, and having hydrolytic activity using p-nitrophenyl-β-D-glucopyranoside as a substrate at least under conditions of a temperature of 85° C. and a pH of 7.5;
(c) a nucleotide sequence that encodes a polypeptide including an amino acid sequence having at least 60% sequence identity with the amino acid sequence represented by SEQ ID NO: 1, and having hydrolytic activity using p-nitrophenyl-β-D-glucopyranoside as a substrate at least under conditions of a temperature of 85° C. and a pH of 7.5;
(d) a nucleotide sequence having at least 80% sequence identity with a nucleotide sequence represented by SEQ ID NO: 2 or 3, and encoding a polypeptide having hydrolytic activity using p-nitrophenyl-β-D-glucopyranoside as a substrate at least under conditions of a temperature of 85° C. and a pH of 7.5; or
(e) a nucleotide sequence of a polynucleotide which hybridizes with a polynucleotide including a nucleotide sequence represented by SEQ ID NO: 2 or 3 under a stringent condition, and being a nucleotide sequence that encodes a polypeptide having hydrolytic activity using p-nitrophenyl-β-D-glucopyranoside as a substrate at least under conditions of a temperature of 85° C. and a pH of 7.5.

[4] The polynucleotide according to the aforementioned aspect [3], wherein the aforementioned polypeptide also has xylanase activity.

[5] An expression vector, which is incorporated with the polynucleotide according to the aforementioned aspect [3] or [4], and which is able to express a polypeptide having β-glucosidase activity in a host cell.

[6] A transformant, which is introduced with the expression vector according to the aforementioned aspect [5].

[7] The transformant according to the aforementioned aspect [6], which is a eukaryotic microbe.

[8] A method for producing a thermostable β-glucosidase, the method including a step of producing the aforementioned thermostable β-glucosidase in the transformant according to the aforementioned aspect [6] or [7].

[9] A glycoside hydrolase mixture, including the thermostable β-glucosidase according to the aforementioned aspect [1] or [2], a thermostable β-glucosidase encoded by the polynucleotide according to the aforementioned aspect [3] or [4], or a thermostable β-glucosidase produced by the method for producing a thermostable β-glucosidase according to the aforementioned aspect [8], and at least one or more types of other glycoside hydrolases.

[10] A method for producing a lignocellulose degradation product, the method including a step of producing a lignocellulose degradation product containing a cellulose degradation product by bringing a material composed of lignocellulose containing cellulose into contact with the thermostable β-glucosidase according to the aforementioned aspect [1] or [2], a thermostable β-glucosidase encoded by the polynucleotide according to the aforementioned aspect [3] or [4], the transformant according to the aforementioned aspect [6] or [7], a thermostable β-glucosidase produced by the method for producing a thermostable β-glucosidase according to the aforementioned aspect [8], or the glycoside hydrolase mixture according to the aforementioned aspect [9].

Effects of the Invention

The thermostable β-glucosidase according to the present invention has hydrolytic activity using PNPG as a substrate at least under conditions of a temperature of 85° C. and a pH of 7.5. For this reason, the aforementioned thermostable β-glucosidase is suitable for a hydrolysis process of materials composed of lignocellulose containing cellulose, for example, materials containing a compound having β-glycosidic bonds, under high temperature conditions.

In addition, the polynucleotide, the expression vector incorporated with the aforementioned polynucleotide and the transformant introduced with the aforementioned expression vector according to the present invention are suitably used for the production of the thermostable β-glucosidase according to the present invention.

BRIEF DESCRIPTION OF THE DRAWINGS

FIG. 1 is a pairwise alignment representation of the amino acid sequence (SEQ ID NO: 1) of a β-glucosidase catalytic domain of a gene clone AR19G-225-3 and the amino acid sequence of a β-glucosidase (SEQ ID NO: 7) of *Thermotoga neapolitana* DSM 4359.

DESCRIPTION OF THE EMBODIMENT

[Thermostable β-glucosidase]

Figure 2:
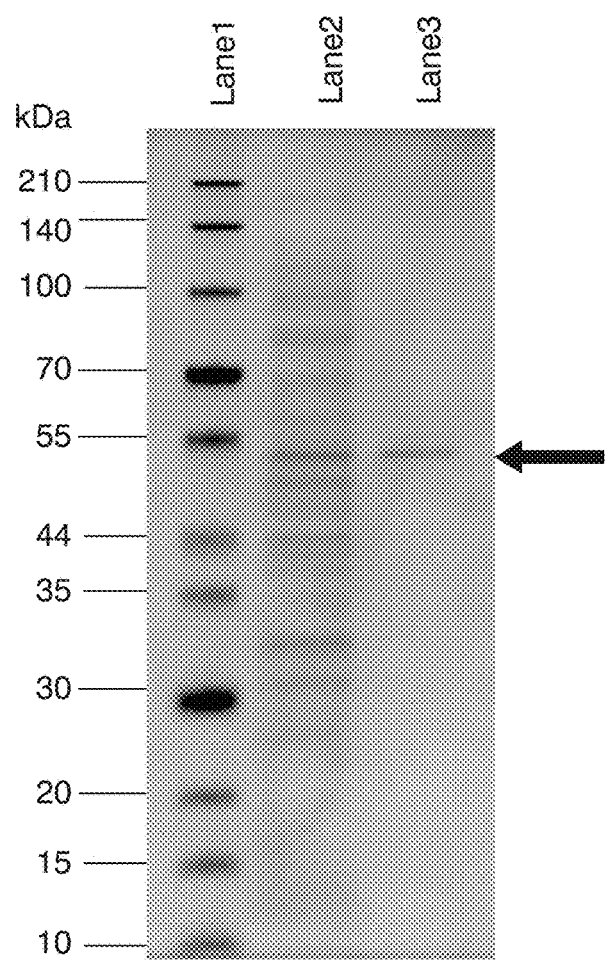
FIG. 2 is a diagram showing the results of SDS-PAGE analysis of the AR19G-225-3 protein obtained by expressing the AR19G-225-3 gene in *E. coli* in Example 1.

Many microorganisms including filamentous fungi, bacteria and archaea are difficult to culture, and about 99% of the microorganisms living in the microbial environments such as soil are said to be unknown microbes. In particular, the culturing of microorganisms living in a high temperature environment is extremely difficult, and it is thought that merely 0.1% or less of the microorganisms living in soils have been isolated and cultured with the currently available microbial culturing techniques. This difficulty to culture such microorganisms living in high temperature soils is one factor to hinder the development of thermostable enzymes.

In recent years, because of the development of the next generation giga sequencer enabling large amount sequencing of giga base pairs, it has become possible to conduct the whole genome sequencing of the microbiota contained in soil and the like. Using this analysis technology, the metagenomic analysis method has been proposed in which the genome DNA of a microbial group is prepared from an environmental sample such as soil, the genomes of the group having nonuniform and miscellaneous genomic organizations are directly and comprehensively sequenced, and the sequenced data are assembled by a parallel computer, so as to thereby reconstruct the genomic sequences of the microbiota. This has contributed to the rapid progress in the genome sequencing of hardly culturable microorganisms.

As shown in Example 1 described later, the inventors of the present invention extracted the genomic DNA (metagenomic DNA) of microbial groups from the collected high temperature hot spring soils (for example, hot spring water of 58 to 90° C. that contains soil, mud, microbial mats, biofilms and the like may be mentioned), and conducted shotgun sequencing and annotation of the metagenomic DNA. By so doing, 104 open reading frames (ORFs) encoding amino acid sequences similar to those of the known β-glucosidase enzymes (for example, amino acid sequences having the Expectation value (i.e. E-value) of less than $1e^{-20}$) were obtained. Of these ORFs, primers were designed based on the nucleotide sequence information of 34 ORFs in which the presence of β-glucosidase catalytic domain could be verified, and gene candidates were cloned from the metagenomic DNA of the high temperature hot spring soils by the PCR method. The PCR-cloned DNAs were incorporated into E. coli, and proteins encoded by the aforementioned nucleotide sequences were expressed. These were subjected to functional screenings by assays on the PNPG degradation activity. In the end, thermostable β-glucosidases having PNPG degradation activity (hereinafter, may be referred to as "AR19G-225-3") were obtained from these ORFs. The amino acid sequence of AR19G-225-3 and the nucleotide sequence encoding the amino acid sequence of AR19G-225-3 are represented by SEQ ID NO: 1 and SEQ ID NO: 3, respectively.

As shown in Example 1 described later, AR19G-225-3 exhibited high hydrolysis activity for PNPG, and also exhibited a certain level of degradation activity for xylan and phosphoric acid swollen Avicel (hereinafter, may be abbreviated as PSA).

From this substrate specificity, AR19G-225-3 is suggested to be a glycoside hydrolase having β-glucosidase activity and also having a certain level of xylanase activity.

It should be noted that in the present invention and the description of this application, the term "β-glucosidase activity" refers to an activity in which by using a compound containing a β-glycosidic bond as a substrate and performing hydrolysis of the substrate, a monosaccharide can be produced.

The "compound containing a β-glycosidic bond" can be exemplified by, for example, a glucan having a β-glycosidic bond, an oligosaccharide having a β-glycosidic bond, and the like.

In addition, in the present invention and the description of this application, the term "xylanase activity" refers to an activity to hydrolyze xylan (xylan hydrolysis activity) by using xylan as a substrate.

Further, in the present invention and the description of this application, the expression "having activity" or "exhibiting activity" refers to an action on at least one substrate and means that a significant difference occurs in the hydrolyzed amount of reducing ends of the substrate or the color reaction as compared to the negative control.

Therefore, the expression "having β-glucosidase activity" refers to an action on at least a compound containing a β-glycosidic bond as a substrate, and means that a significant difference occurs in the hydrolyzed amount of the reducing ends of the substrate or the color reaction as compared to the negative control.

In addition, as another aspect, the expression "having β-glucosidase activity" refers to an action on at least PNPG as a substrate, and means that a significant difference occurs in the hydrolyzed amount of the reducing ends of the substrate or the color reaction as compared to the negative control.

The expression "having xylanase activity" refers to an action on at least xylan as a substrate, and means that a significant difference occurs in the hydrolyzed amount of reducing ends of the substrate or the color reaction as compared to the negative control.

In addition, as yet another aspect, the expression "having β-glucosidase activity" means having 15 U/mg protein or more hydrolytic activity for at least PNPG under condition of a pH of 7.5 and in a temperature range of 70 to 90° C.

Further, as yet another aspect, the expression "having β-glucosidase activity" means having 5 U/mg protein or more hydrolytic activity for at least PNPG under condition of a temperature of 70 to 85° C. and in a pH range of 5.0 to 9.0.

In addition, the amino acid sequence of AR19G-225-3 was searched in publicly known amino acid sequence databases, resulting that the amino acid sequence showing the highest sequence identity was of a β-glucosidase A (Genbank Registration ID: ACM22958.1) (SEQ ID NO: 7) of *Thermotoga neapolitana* DSM 4359, and the sequence identity (homology) thereof was only 55%. From the substrate specificity and the sequence identity of the amino acid sequence with that of the already known proteins, it is clear that AR19G-225-3 is a novel β-glucosidase.

AR19G-225-3 has hydrolytic activity using PNPG as a substrate at least under conditions of a temperature of 85° C. and a pH of 7.5. Actually, as shown in Example 1 <8> described later, AR19G-225-3 exhibits β-glucosidase activity within a temperature range from 50 to 100° C. under a condition of a pH of 7.5, and also exhibits strong β-glucosidase activity within a temperature range from 70 to 90° C. More specifically, the β-glucosidase activity of AR19G-225-3 tended to be increased as the temperature was increased within a range from 50 to 85° C. and tended to be decreased rapidly when the temperature exceeded 90° C., under a condition of a pH of 7.5.

Generally, in a protein having some kind of bioactivity, one or two or more amino acids can be deleted, substituted, or added, without deteriorating the bioactivity. In other words, also in AR19G-225-3, one or two or more amino acids can be deleted, substituted, or added, without causing loss of glycoside hydrolytic activity, including β-glucosidase activity.

That is, the thermostable β-glucosidase according to the present invention is a thermostable β-glucosidase having a β-glucosidase catalytic domain which includes any one of the following (A) to (C):

(A) A polypeptide including an amino acid sequence represented by SEQ ID NO: 1 (that is, AR19G-225-3);

(B) a polypeptide including an amino acid sequence in which at least one amino acid is deleted, substituted, or added in the amino acid sequence represented by SEQ ID NO: 1, as well as having hydrolytic activity using PNPG as a substrate at least under conditions of a temperature of 85° C. and a pH of 7.5; or (C) a polypeptide including an amino acid sequence having at least 60% sequence identity with the amino acid sequence represented by SEQ ID NO: 1, as well as having hydrolytic activity using PNPG as a substrate at least under conditions of a temperature of 85° C. and a pH of 7.5.

In the present invention and the description of this application, a "polypeptide in which an amino acid is deleted" means that a portion of the amino acids which constitute the polypeptide is missing (that is, removed).

In the present invention and the description of this application, a "polypeptide in which an amino acid is substituted" means that an amino acid which constitutes the polypeptide is replaced with a different amino acid.

In the present invention and the description of this application, a "polypeptide in which an amino acid is added" means that a new amino acid is inserted within the polypeptide.

In the aforementioned polypeptide of (B), the number of amino acids to be deleted, substituted, or added in the amino acid sequence represented by SEQ ID NO: 1 is preferably from 1 to 20, more preferably from 1 to 10, and still more preferably from 1 to 5.

In the aforementioned polypeptide of (C), the sequence identity with the amino acid sequence represented by SEQ ID NO: 1 is not particularly limited as long as it is 60% or greater but less than 100%, although it is preferable to be 70% or greater but less than 100%, more preferably 75% or greater but less than 100%, and still more preferably 80% or greater but less than 100%. In particular, the sequence identity with the amino acid sequence represented by SEQ ID NO: 1 in the aforementioned polypeptide of (C) is preferably 85% or greater but less than 100%, more preferably 90% or greater but less than 100%, still more preferably 95% or greater but less than 100%, and particularly preferably 98% or greater but less than 100%.

It should be noted that the sequence identity (homology) between a pair of amino acid sequences is obtained such that: two amino acid sequences are juxtaposed while having gaps in some parts accounting for insertion and deletion so that the largest numbers of corresponding amino acids can be matched, and the sequence identity is deemed to be the proportion of the matched amino acids relative to the whole amino acid sequences excluding the gaps, in the resulting alignment. The sequence identity between a pair of amino acid sequences can be obtained by using a variety of homology search software publicly known in the art. The sequence identity value between amino acid sequences in the present invention is obtained by calculation on the basis of an alignment obtained from a publicly known homology search software BLASTP.

The aforementioned polypeptides of (B) and (C) may be those that are artificially designed, or may also be homologues of AR19G-225-3 and the like, or partial proteins thereof.

The aforementioned polypeptides of (A) to (C) may be respectively synthesized in a chemical manner based on the amino acid sequence, or may also be produced by a protein expression system using the polynucleotide according to the present invention that will be described later. In addition, the aforementioned polypeptides of (B) and (C) can also be respectively synthesized artificially based on a polypeptide including the amino acid sequence represented by SEQ ID NO: 1, by using a genetic recombination technique to introduce amino acid mutation(s).

The aforementioned polypeptides of (A) to (C) have hydrolysis activities (that is, β-glucosidase activity) using PNPG as a substrate at least under conditions of a temperature of 85° C. and a pH of 7.5. For this reason, a thermostable β-glucosidase can be obtained by having any one of the aforementioned polypeptides of (A) to (C) as the β-glucosidase catalytic domain.

The thermostable β-glucosidase according to the present invention uses PNPG as a substrate. In addition to PNPG, the aforementioned thermostable β-glucosidase may also use another type of β-glucan other than PNPG, an oligosaccharide, or the like as a substrate. Examples of those that can also be used as a substrate by the thermostable β-glucosidase according to the present invention other than PNPG include p-nitrophenyl-β-D-xylopyranoside (hereinafter, may be abbreviated as PNPX); a glucan composed of β-1,3 bonds and β-1,4 bonds such as lichenan; xylan; a crystalline cellulose, such as Avicel, a bacterial crystalline cellulose (bacterial microcrystalline cellulose, BMCC) and a filter paper; PSA; carboxymethyl cellulose (hereinafter, may be abbreviated as CMC); a glucan composed of β-1,4 bonds; an oligosaccharide composed of β-1,4 bonds such as cellobiose; a glucan composed of β-1,3 bonds and β-1,6 bonds such as laminarin; a glucan composed of β-1,3 bonds; a glucan composed of β-1,6 bonds; and an oligosaccharide composed of β-1,6 bonds such as gentiobiose. As the thermostable β-glucosidase according to the present invention, a thermostable β-glucosidase that also uses, in addition to PNPG, at least one member selected from the group consisting of PNPX, PSA, and xylan as a substrate is preferred.

The thermostable β-glucosidase according to the present invention preferably exhibits hydrolytic activity (β-glucosidase activity) using PNPG as a substrate at least under conditions of a pH of 7.5 within a temperature range from 70 to 90° C., more preferably within a temperature range from 60 to 90° C., and still more preferably within a temperature range from 50 to 100° C. The optimum temperature of the thermostable β-glucosidase according to the present invention is preferably within the range from 70 to 90° C., more preferably within the range from 80 to 90° C.

Although the optimum pH of the thermostable β-glucosidase according to the present invention varies depending on the reaction temperature, it is within a pH range from 6.0 to 8.5. As the thermostable β-glucosidase according to the present invention, those exhibiting β-glucosidase activity at least within a pH range of 5.0 to 9.0 are preferred, and those exhibiting β-glucosidase activity within a pH range of 4.0 to 9.5 are more preferred.

The thermostable β-glucosidase according to the present invention may also have, in addition to the aforementioned thermostable β-glucosidase activity, another type of cellulose hydrolysis activity other than the β-glucosidase activity. Such another type of cellulose hydrolysis activity other than the aforementioned thermostable β-glucosidase activity can be exemplified by endoglucanase activity, xylanase activity, xylosidase activity, cellobiohydrolase activity, and the like, and xylanase activity is preferred.

The thermostable β-glucosidase according to the present invention may be an enzyme solely consisting of a β-glucosidase catalytic domain which includes any one of the aforementioned polypeptides of (A) to (C), or may further include other domains. Examples of other domains include a domain present in the known β-glucosidases other than the β-glucosidase catalytic domain. For example, the thermostable β-glucosidase according to the present invention also includes enzymes obtained by substituting a β-glucosidase catalytic domain in a publicly known β-glucosidase with the aforementioned polypeptides of (A) to (C).

If the thermostable β-glucosidase according to the present invention further includes, in addition to the β-glucosidase catalytic domain, a domain other than the β-glucosidase catalytic domain, it is preferable to include a cellulose-binding module. The cellulose-binding module may be either on the upstream (N-end side) or the downstream (C-end side) of the β-glucosidase catalytic domain. In addition, the cellulose-binding module and the β-glucosidase catalytic domain may be directly linked, or linked via a linker domain of an appropriate length. The thermostable β-glucosidase according to the present invention is preferably such that the cellulose-binding module is present on the upstream or the downstream of the β-glucosidase catalytic domain via a linker domain, more preferably such that the cellulose-binding module is present on the upstream of the β-glucosidase catalytic domain via a linker domain.

The cellulose-binding module contained in the thermostable β-glucosidase according to the present invention may suffice if it is a domain having an ability to bind to cellulose, for example, a domain having an ability to bind to PSA or a crystalline Avicel. The amino acid sequence thereof is not particularly limited. As the cellulose-binding module, for example, a cellulose-binding module of an already known protein or appropriately modified product thereof may be used. In addition, if the thermostable β-glucosidase according to the present invention has a β-glucosidase catalytic domain and a cellulose-binding module, it is preferable that these are linked via a linker sequence. The amino acid sequence, the length, and the like, of the linker sequence are not particularly limited.

In addition, the thermostable β-glucosidase according to the present invention may also have a signal peptide enabling to transport it to a specific region to effect localization within a cell, or a signal peptide to effect extracellular secretion, at the N end or the C end. Such a signal peptide can be exemplified by an apoplastic transport signal peptide, an endoplasmic reticulum retention signal peptide, a nuclear transport signal peptide, a secretory signal peptide, or the like. The endoplasmic reticulum retention signal peptide can be exemplified by, for example, a signal peptide including a HDEL amino acid sequence, or the like. In those cases where the thermostable β-glucosidase according to the present invention has a signal peptide at the N end or the C end, the thermostable β-glucosidase expressed in a transformant can be secreted outside the cell, or can be localized in the intracellular endoplasmic reticulum, or the like.

In addition, the thermostable β-glucosidase according to the present invention may also be added with, for example, various types of tags at the N end or the C end of the thermostable β-glucosidase, so as to enable easy and convenient purification in a case of the production using an expression system. Regarding such a tag, for example, it is possible to use a tag for usual use in the expression or purification of a recombinant protein, such as a His tag, a HA (hemagglutinin) tag, a Myc tag, and a Flag tag.

[Polynucleotide that Encodes Thermostable β-Glucosidase]

The polynucleotide according to the present invention encodes the thermostable β-glucosidase according to the present invention. The aforementioned thermostable β-glucosidase can be produced by using the expression system of a host made by introducing an expression vector incorporated with the polynucleotide into the host.

More specifically, the polynucleotide according to the present invention is a polynucleotide having a region that encodes a β-glucosidase catalytic domain which includes any one of the following nucleotide sequences (a) to (e).

(a) A nucleotide sequence that encodes a polypeptide including the amino acid sequence represented by SEQ ID NO: 1;

(b) a nucleotide sequence that encodes a polypeptide including an amino acid sequence in which at least one amino acid is deleted, substituted, or added in the amino acid sequence represented by SEQ ID NO: 1, as well as having hydrolytic activity using PNPG as a substrate at least under conditions of a temperature of 85° C. and a pH of 7.5;

(c) a nucleotide sequence that encodes a polypeptide including an amino acid sequence having at least 60% sequence identity with the amino acid sequence represented by SEQ ID NO: 1, as well as having hydrolytic activity using PNPG as a substrate at least under conditions of a temperature of 85° C. and a pH of 7.5;

(d) a nucleotide sequence having at least 80% sequence identity with a nucleotide sequence represented by SEQ ID NO: 2 or 3, as well as encoding a polypeptide having hydrolytic activity using PNPG as a substrate at least under conditions of a temperature of 85° C. and a pH of 7.5; or (e) a nucleotide sequence of a polynucleotide which hybridizes with a polynucleotide including a nucleotide sequence represented by SEQ ID NO: 2 or 3 under a stringent condition, as well as being a nucleotide sequence that encodes a polypeptide having hydrolytic activity using PNPG as a substrate at least under conditions of a temperature of 85° C. and a pH of 7.5.

It should be noted that in the present invention and the description of this application, a "polynucleotide in which a nucleotide is deleted" means that a portion of the nucleotides which constitute the polynucleotide is missing (that is, removed).

In the present invention and the description of this application, a "polynucleotide in which a nucleotide is substituted" means that a nucleotide which constitutes the polynucleotide is replaced with a different nucleotide.

In the present invention and the description of this application, a "polynucleotide in which a nucleotide is added" means that a new nucleotide is inserted within the polynucleotide.

In the present invention and the description of this application, the term "under a stringent condition" can be exemplified by the method described in Molecular Cloning—A Laboratory Manual Third Edition (Sambrook et al., Cold Spring Harbor Laboratory Press). The example thereof includes a condition in which hybridization is performed by incubation in a hybridization buffer including 6×SSC (composition of 20×SSC: 3M sodium chloride, 0.3M citric acid solution, and pH7.0), 5×Denhardt's solution (composition of 100×Denhardt's solution: 2 mass % bovine serum albumin, 2 mass % Ficoll, 2 mass % polyvinylpyrrolidone), 0.5 mass % SDS, 0.1 mg/mL salmon sperm DNA, and 50% formamide, at a temperature of 42 to 70° C. for several hours to overnight. The washing buffer for use in the washing after the incubation is preferably 1×SSC solution containing 0.1 mass % SDS, and more preferably 0.1×SSC solution containing 0.1 mass % SDS.

In the aforementioned nucleotide sequences of (a) to (e), it is preferable to select a degenerate codon having high frequency of usage in the host. For example, the aforementioned nucleotide sequence of (a) may be a nucleotide sequence represented by SEQ ID NO: 2, may be a nucleotide sequence represented by SEQ ID NO: 3, or may be a nucleotide sequence altered to have a codon having high frequency of usage in the host without changing the amino acid sequence to be encoded by the nucleotide sequence represented by SEQ ID NO: 2 or 3. Note that, these codons can be altered by a publicly known gene sequence modification technique or artificial gene synthesis.

The polynucleotide including the nucleotide sequence represented by SEQ ID NO: 2 or 3 may be synthesized in a chemical manner based on the nucleotide sequence information, or may be obtained as a full length of a gene that encodes AR19G-225-3 (may be referred to as "AR19G-225-3 gene" or "gene clone AR19G-225-3") or a partial region thereof including the β-glucosidase catalytic domain from the natural world by using a genetic recombination technique. The full length of the AR19G-225-3 gene or the partial region thereof can be obtained by, for example, collecting a sample containing microorganisms from the natural world, and conducting PCR using the genomic DNA recovered from the sample as a template, with a forward primer and a reverse primer designed on the basis of the nucleotide sequence represented by SEQ ID NO: 2 or 3 by a conventional method. The cDNA synthesized by a reverse transcription reaction using mRNA recovered from the sample as a template may also be used as a template. Note that, it is preferable that the sample for recovering the nucleic acid serving as a template is a sample collected from a high temperature environment such as hot spring soil.

In the aforementioned nucleotide sequence of (d), the sequence identity with the nucleotide sequence represented by SEQ ID NO: 2 or 3 is not particularly limited as long as it is 80% or greater but less than 100%, although it is preferable to be 85% or greater but less than 100%, more preferably 90% or greater but less than 100%, and still more preferably 95% or greater but less than 100%.

Note that, the sequence identity (homology) between a pair of nucleotide sequences is obtained such that: two nucleotide sequences are juxtaposed while having gaps in some parts accounting for insertion and deletion so that the largest numbers of corresponding nucleotides can be matched, and the sequence identity is deemed to be the proportion of the matched nucleotides relative to the whole nucleotide sequences excluding gaps, in the resulting alignment. The sequence identity between a pair of nucleotide sequences can be obtained by using a variety of homology search software publicly known in the art. The sequence identity value between nucleotide sequences in the present invention is obtained by calculation on the basis of an alignment obtained from a publicly known homology search software BLASTN.

For example, the polynucleotide including the aforementioned nucleotide sequence of (b), (c), or (d) can be respectively synthesized artificially by deleting, substituting, or adding one or two or more nucleotides in a polynucleotide including the nucleotide sequence represented by SEQ ID NO: 2 or 3. In addition, the aforementioned nucleotide sequence of (b), (c), or (d) may also be a full length sequence of a homologous gene of the AR19G-225-3 gene or a partial sequence thereof. The homologous gene of the AR19G-225-3 gene can be obtained by a genetic recombination technique for use in obtaining a homologous gene of a gene whose nucleotide sequence has been already known.

The polynucleotide according to the present invention may have only the region that encodes the β-glucosidase catalytic domain, or may also have a region that encodes a cellulose-binding module, a linker sequence, various types of signal peptides, various types of tags, or the like, in addition to the aforementioned region.

[Expression Vector]

The expression vector according to the present invention is incorporated with the aforementioned polynucleotide according to the present invention, and is able to express a polypeptide (β-glucosidase) having hydrolytic activity using PNPG as a substrate at least under conditions of a temperature of 85° C. and a pH of 7.5 in a host cell. That is, it is an expression vector which is incorporated with the aforementioned polynucleotide according to the present invention in a state where the aforementioned thermostable β-glucosidase according to the present invention can be expressed. More specifically, it is necessary for the expression vector to be incorporated with an expression cassette including, from the upstream, DNA having a promoter sequence, the aforementioned polynucleotide according to the present invention, and DNA having a terminator sequence. It should be noted that the incorporation of the polynucleotide into the expression vector can be performed by using a well-known genetic recombination technique. It is also possible to use a commercially available expression vector preparation kit for the incorporation of the polynucleotide into the expression vector.

In the present invention and the description of this application, an "expression vector" is a vector including, from the upstream, DNA having a promoter sequence, DNA having a sequence for incorporating foreign DNA, and DNA having a terminator sequence.

The expression vector may be a vector to be introduced into a prokaryotic cell such as *E. coli*, or to be introduced into a eukaryotic cell such as a yeast, a filamentous fungus, a cultured insect cell, a cultured mammalian cell, or a plant cell. Regarding such an expression vector, an arbitrary expression vector for usual use can be adopted corresponding to the respective host.

It is preferable that the expression vector according to the present invention is an expression vector incorporated with not only the aforementioned polynucleotide according to the present invention but also a drug resistance gene or the like. This is because it makes it easy to screen host cells transformed by the expression vector and untransformed host cells.

The drug resistance gene can be exemplified by a kanamycin resistance gene, a hygromycin resistance gene, a bialaphos resistance gene, or the like.

[Transformant]

The transformant according to the present invention is introduced with the above-mentioned expression vector according to the present invention. In the aforementioned transformant, the thermostable β-glucosidase according to the present invention can be expressed. The host to introduce the expression vector may be a prokaryotic cell such as *E. coli* or a eukaryotic cell such as a yeast, a filamentous fungus, a cultured insect cell, a cultured mammalian cell, or a plant cell. That is, the transformant according to the present invention is *E. coli*, a yeast, a filamentous fungus, a cultured insect cell, a cultured mammalian cell, a plant cell, or the like which is introduced with the expression vector according to the present invention. By culturing a transformant of *E. coli*, the thermostable β-glucosidase according to the present invention can be produced more easily and conveniently with high yield. On the other hand, because proteins are glycosylated in eukaryotic cells, a thermostable β-glucosidase which is more thermostable can be produced by using a transformant of a eukaryotic cell rather than by using a transformant of a prokaryotic cell.

The method to produce the transformant using the expression vector is not particularly limited, and a method for usual use in the production of transformants can be conducted. The concerned method can be exemplified by an *Agrobacterium*-mediated method, a particle gun method, an electroporation method, a PEG (polyethylene glycol) method, and the like. Of these, if the host is a plant cell, a particle gun method or an *Agrobacterium*-mediated method is preferred.

If a prokaryotic cell, a yeast, a filamentous fungus, a cultured insect cell, a cultured mammalian cell, or the like is used as a host, the obtained transformant is generally able to be cultured by a usual method in the same manner as that of the untransformed host.

[Method for Producing a Thermostable β-Glucosidase]

The method for producing a thermostable β-glucosidase according to the present invention is a method to produce a thermostable β-glucosidase in the aforementioned transformant according to the present invention. When culturing a transformant produced by using the expression vector incorporated with the aforementioned polynucleotide according to the present invention on the downstream of a promoter which has no ability to regulate the timing of the expression or the like, in the transformant, the thermostable β-glucosidase according to the present invention is expressed constitutively. On the other hand, for the transformant produced by using a so-called expression inducible promoter to induce the expression by means of a specific compound, temperature condition, or the like, the thermostable β-glucosidase is expressed in the concerned transformant by culturing the transformant and conducting an induction treatment suitable for the respective expression-inducing condition.

The thermostable β-glucosidase produced by the transformant may be used in a state of being retained in the transformant, or may be extracted/purified from the transformant.

The method to extract or purify the thermostable β-glucosidase from the transformant is not particularly limited as long as the method does not deteriorate the activity of the thermostable β-glucosidase, and the extraction can be done by a method for usual use in the extraction of a polypeptide from cells or biological tissues. The method can be exemplified by a method in which the transformant is immersed in an appropriate extraction buffer to extract the thermostable β-glucosidase, and thereafter the liquid extract and the solid residue are separated. The extraction buffer preferably contains a solubilizing agent such as a surfactant. If the transformant is a plant, the transformant may be previously shredded or crushed before immersing in an extraction buffer. Moreover, as the method for separating the liquid extract and the solid residue, for example, a publicly known solid-liquid separation treatment such as a filtration method, a compression filtration method, or a centrifugation treatment method may be used, or the transformant immersed in an extraction buffer may be squeezed. The thermostable β-glucosidase in the liquid extract can be purified by using a publicly known purification method such as a salting-out method, an ultrafiltration method, or a chromatography method.

If the thermostable β-glucosidase according to the present invention is expressed while the secretory signal peptide is held in the transformant, a solution containing the thermostable β-glucosidase can be easily and conveniently obtained by culturing the transformant and thereafter recovering a culture liquid supernatant made by removal of the transformant from the obtained culture product. Moreover, if the thermostable β-glucosidase according to the present invention has a tag such as a His tag, the thermostable β-glucosidase in a liquid extract or in a culture supernatant can be easily and conveniently purified by an affinity chromatography method using the tag.

In other words, the method for producing a thermostable β-glucosidase according to the present invention includes the culturing of the transformant according to the present invention to produce a thermostable β-glucosidase within the transformant, and, according to need, the extraction and purification of the thermostable β-glucosidase from the transformant.

[Glycoside Hydrolase Mixture]

The glycoside hydrolase mixture according to the present invention can also be used as a mixture containing the aforementioned thermostable β-glucosidase according to the present invention, or a thermostable β-glucosidase produced by the aforementioned method for producing a thermostable β-glucosidase according to the present invention, and at least one or more types of other glycoside hydrolases. The thermostable β-glucosidase produced by the aforementioned method for producing a thermostable β-glucosidase according to the present invention may be in a state of being included in the transformant, or may be extracted or purified from the transformant. By using the thermostable β-glucosidase according to the present invention as a mixture with other glycoside hydrolases in the reaction to degrade a material composed of lignocellulose containing cellulose, the material composed of lignocellulose containing persistent cellulose can be more efficiently degraded.

The other glycoside hydrolase than the aforementioned thermostable β-glucosidase to be contained in the glycoside hydrolase mixture is not particularly limited as long as it has hydrolysis activity for cellulose or hemicellulose. The other glycoside hydrolase than the aforementioned β-glucosidase to be contained in the glycoside hydrolase mixture can be exemplified by hemicellulases such as xylanase or β-xylosidase, cellobiohydrolase, β-glucosidase, endoglucanase, or the like. In addition to the thermostable β-glucosidase, the glycoside hydrolase mixture according to the present invention is preferably a mixture further containing at least either one of glycoside hydrolases (i.e., a hemicellulase or an endoglucanase), and more preferably a mixture containing both of glycoside hydrolases (i.e., a hemicellulase and an endoglucanase). Among them, a mixture further containing, in addition to the thermostable β-glucosidase, at least one of glycoside hydrolases selected from the group consisting of xylanase, β-xylosidase, cellobiohydrolase, and endoglucanase is preferred; and a mixture containing all of glycoside hydrolases (i.e., xylanase, β-xylosidase, cellobiohydrolase, and endoglucanase) is more preferred.

The other glycoside hydrolase to be contained in the glycoside hydrolase mixture is preferably a thermostable glycoside hydrolase having glycoside hydrolysis activity at least at a temperature of 85° C., and more preferably a thermostable glycoside hydrolase having glycoside hydrolysis activity at a temperature of 70 to 90° C. When all the enzymes contained in the glycoside hydrolase mixture are thermostable (for example, the optimum temperature of the enzyme activity or the thermal denaturation temperature of the enzyme protein is 70° C. or higher), the reaction to degrade the material composed of lignocellulose containing cellulose with the glycoside hydrolase mixture can be efficiently conducted under a high temperature condition. That is, if the glycoside hydrolase mixture contains only thermostable glycoside hydrolases, it becomes possible, by using the glycoside hydrolase mixture for the hydrolysis process of a material composed of lignocellulose containing cellulose, to conduct the hydrolysis reaction of the material composed of lignocellulose containing cellulose under a high temperature environment where the hydrolysis temperature is from 70 to 90° C. (high temperature hydrolysis). With this high temperature hydrolysis, the amount of enzymes and the time for hydrolysis can be remarkably reduced, and the cost for hydrolysis can be largely cut out.

[Method for Producing a Lignocellulose Degradation Product]

The method for producing a lignocellulose degradation product according to the present invention is a method to degrade a material composed of lignocellulose containing cellulose, for example, a material containing a compound with a β-glycosidic bond, to thereby obtain the degradation product thereof, with the thermostable β-glucosidase according to the present invention. More specifically, a material composed of lignocellulose containing cellulose, for example, a material containing a compound with a β-glycosidic bond is brought into contact with the thermostable β-glucosidase according to the present invention, the transformant according to the present invention, a thermostable β-glucosidase produced by the method for producing a thermostable β-glucosidase according to the present invention, or the glycoside hydrolase mixture according to the present invention. By doing so, a lignocellulose degradation product, for example, a degradation product of cellulose (for example, a degradation product in a state where the β-glycosidic bonds in the aforementioned material have been fully or partially degraded, and such a degradation product can be exemplified by monosaccharide such as glucose and xylose, oligosaccharide consisting of such the monosaccharide, and the like) is produced.

The material composed of lignocellulose containing cellulose, for example, the material containing a compound with a β-glycosidic bond, is not particularly limited as long as it contains cellulose, for example, a compound containing a β-glycosidic bond. Such a material can be exemplified by cellulose-based biomass such as a weed and an agricultural waste, used paper, or the like. The above material is preferably subjected to a physical treatment such as crushing or shredding, a chemical treatment with an acid, alkali, or the like, or a treatment such as immersing in an appropriate buffer or a dissolution treatment, or the like, prior to being brought into contact with the thermostable β-glucosidase according to the present invention.

The reaction condition of the hydrolysis reaction of the material composed of lignocellulose containing cellulose, for example, the material containing a compound with a β-glycosidic bond by means of the thermostable β-glucosidase according to the present invention may suffice if the condition allows the thermostable β-glucosidase to exhibit β-glucosidase activity. For example, it is preferable to conduct the reaction at a temperature of 60 to 90° C. and a pH of 5.0 to 9.0, more preferable to conduct the reaction at a temperature of 70 to 90° C. and a pH of 5.0 to 9.0, and still more preferable to conduct the reaction at a temperature of 70 to 90° C. and a pH of 6.0 to 8.5. The reaction time of the hydrolysis reaction is appropriately adjusted in consideration of the type, the method of pretreatment, the amount, or the like, of the material composed of lignocellulose containing cellulose to be supplied to the hydrolysis.

For example, the hydrolysis reaction can be carried out in a reaction time of 10 minutes to 100 hours, and 1 to 100 hours when degrading the cellulose-based biomass.

For the hydrolysis reaction of the aforementioned material composed of lignocellulose containing cellulose, it is also preferable to use at least one or more types of other glycoside hydrolases simultaneously or separately, in addition to the thermostable β-glucosidase according to the present invention. The other glycoside hydrolase may be the same as the glycoside hydrolase that can be contained in the aforementioned glycoside hydrolase mixture, and it is preferable to be a thermostable glycoside hydrolase having glycoside hydrolysis activity at least at a temperature of 85° C., and preferably at least at a temperature of 70 to 90° C. In addition, one aspect of the method for producing a lignocellulose degradation product is the use of the thermostable β-glucosidase according to the present invention, the transformant according to the present invention, or a thermostable β-glucosidase produced by the method for producing a thermostable β-glucosidase according to the present invention, and another aspect is the use of the aforementioned glycoside hydrolase mixture.

EXAMPLES

Next is a more detailed description of the present invention with reference to Examples. However, the present invention is not to be limited to the following Examples.

Example 1

Cloning of Novel Thermostable β-Glucosidase from Hot Spring Soil

<1> DNA Extraction from Hot Spring Soil and Whole Genome Sequencing (WGS)

With the purpose of searching for genes of novel thermostable β-glucosidase exhibiting activity at a temperature of 70 to 90° C., soil DNA was collected from neutral to weakly alkaline hot springs and subjected to nucleotide sequencing of the metagenomic DNA of the microbiota constituting the soil.

As the soil sample from neutral to weakly alkaline hot springs, hot spring water containing soil, clay, and biomat was collected from five sampling points having gushing high temperature outdoor hot springs in three areas in Japan (metagenomic DNA samples N2, AR19, AR15, OJ1, and H1). These hot spring soil samples were within a range of temperature from 58 to 78° C. and a pH of 7.2 to 8 at the time of the collection.

DNA was extracted from 10 g of each of the collected hot spring soil samples by using the DNA extraction kit (ISOIL Large for Beads ver. 2, manufactured by NIPPON GENE Co., Ltd.). 5 μg of the extracted DNA was subjected to shotgun sequencing of the metagenomic DNA by using the sequencer GS FLX Titanium 454 manufactured by Roche Diagnostics K.K. The remaining DNA was used for PCR cloning of the β-glucosidase gene.

The metagenomic DNA sequencing was carried out using the hot spring soil sample AR19. By so doing, a data set of the whole genome sequence (WGS) with an average read length of 396 bp, a total read number of 2,766,332, and a total quantity of sequenced genomes of 1,106,243,280 bp, was obtained.

<2> Assembling and Statistics of Hot Spring Metagenomic Data

The output from the Roche 454 (sff file) was rebasecalled with the PyroB ayes (Quinlan et al., Nature Methods, 2008, vol. 5, p. 179-81.), by which sequence files and quality files in FASTA format were obtained. After clipping their ends to improve the quality, the obtained sequence reads were assembled with use of the assembly software, Newbler version 2.3 of 454 Life Sciences. The assembling was performed by setting "minimum acceptable overlap match (mi)=0.9", and "option:-large (for large or complex genomes, speeds up assembly, but reduces accuracy.)".

The total of the quality filter processed reads and 100 by or longer assemble contigs was 104,096,316 bp. This data set was used for the glycoside hydrolase gene analysis. Out of the total read number of 2,766,332 reads, 2,308,679 reads were assembled into 1,027 by or longer contigs in average (101,372 contigs in total). Of these, the longest contig length was 187,970 bp.

<3>Prediction of open reading frames (ORFs) of β-glucosidase

The sequences of EC numbers of 3.2.1.4 (cellulase), 3.2.1.21 (β-glucosidase), .2.1.37 (β-glucosidase), 3.2.1.91 (cellulose 1,4-β-cellobiosidase), and 3.2.1.8 (endo 1,4β-xylanase) were obtained from the UniProt database, and the proteome local database of these glycoside hydrolase genes was constructed. Using the annotation software Orphelia (Hoff et al., Nucleic Acids Research, 2009, 37 (Web Server issue: W101-W105), gene regions (=open reading frames) were predicted from the contig sequences obtained from the above-mentioned process <2>. In order to extract the glycoside hydrolase gene from the predicted ORF, the aforementioned local database using BLASTP (blastall ver. 2.2.18) was referred to. Optional conditions of BLASTP were set such that: "Filter query sequence =false", "Expectation value (E) <1e-20" [hereunder, the default values: Cost to open a gap =-1, Cost to extended gap =-1, X dropoff value for gapped alignment =0, Threshold for extending hits =0, and Word size =default], and the ORF sequences that hit any one of Glyco$_{13}$hydro$_{13}3_{13}$C, Exo-1,4-beta glucosidase, Beta-glucosidase, B-glucosidase, Xylosidase, Glycoside hydrolase family 1, Glycoside hydrolase family 3, Glycoside hydrolase family 1, Glycoside hydrolase family 3, Beta-D-glucoside glucohydrolase, and Beta-galactosidase that were entered in the aforementioned local database were collected as candidate sequences of β-glucosidase.

<4> Classification of Genes into Glycoside Hydrolase (GH) Families

The candidate sequences of β-glucosidase that had been collected in the above-mentioned process <3> were subjected to functional classification, with reference to the protein functional region sequence database of pfam HMMs (Pfam version 23.0 and HMMER v2.3; Finn et al., Nucleic Acids Research Database, 2010, Issue 38, p. D211-222). More specifically, the glycoside hydrolase (GH) families were determined by the homology with the Pfam domain database by using the sequence homology search algorithm HMMER to which the hidden Markov model was applied (Durbin et al., "The theory behind profile HMMs. Biological sequence analysis: probabilistic models of proteins and nucleic acids", 1998, Cambridge University Press; hmmpfam (Ver. 2.3.2), E-value cutoff<1e-5; Database=Pfam_fs (models that can be used to find fragments of the represented domains in a sequence.)).

The result of the GH family classification of 104 ORFs predicted as candidate sequences of β-glucosidase is shown in Table 1. Those that covered 70% or more of the sequence of GH catalytic domain were counted. The sequences exhibiting a coverage of the GH catalytic domain of less than 70% and the sequences whose homologues could not be found in the Pfam database were classified as unknown GH. As shown in Table 1,10β-glucosidase ORFs belonging to the GH1 family were obtained. On the other hand, 19β-glucosidase ORF sequences belonging to the GH3 family, 4β-glucosidase ORFs belonging to the GH31 family, and 1β-glucosidase ORF belonging to the GH43 family were obtained, respectively. Primers were designed for all of these 34 ORFs including incomplete sequences in which the presence of β-glucosidase catalytic domain sequences could be confirmed and these genes were cloned from the hot spring soil metagenomic DNA by PCR. In the ORF prediction by the Orphelia software, initiation codons (L, V) other than methionine (M) were predicted at times, and the number of full-length ORFs indicated in Table 1 also includes ORFs with these initiation codons. In Table 1, the number in the brackets shows the number of full-length ORFs having methionine as the initiation codon. Although the presence of a gene having an initiation codon other than methionine had been reported, since the ratio thereof was high from the results of Table 1, it was considered to contain a lot of false positives. For ORFs in which initiation codons were not methionine, primers were designed so as to add the codon sequence of methionine (ATG) to the 3' end of the sequence.

TABLE 1

| AR19 metagenome | GH family classification of β-glucosidase genes | | | | | | |
|---|---|---|---|---|---|---|---|
| | GH1 | GH3 | GH31 | GH43 | Other GHs | Unknown GHs | Total |
| Full-length ORFs | 8(6) | 12(9) | 3(3) | 1(1) | 0 | 31(22) | 55(41) |
| Incomplete ORFs | 2 | 7 | 1 | 0 | 0 | 39 | 49 |
| Total number of ORFs | 10 | 19 | 4 | 1 | 0 | 70 | 104 |

<5> Open Reading Frame AR19G-225

The open reading frame AR19G-225 encoded a polypeptide (SEQ ID NO: 1) including 442 amino acid residues and was a full-length sequence (SEQ ID NO: 2), such that the polypeptide started from methionine which was an amino acid residue at position 1, and the 3' end of the nucleotide sequence encoding the polypeptide ended with a termination codon. From the sequence homology of motifs, 441 amino acids from glutamine (Q) at position 2 to serine (S) at the end at position 442 in the polypeptide encoded by the open reading frame AR19G-225 were predicted to be a catalytic domain of the Glycoside hydrolase family 1.

Figure 1:
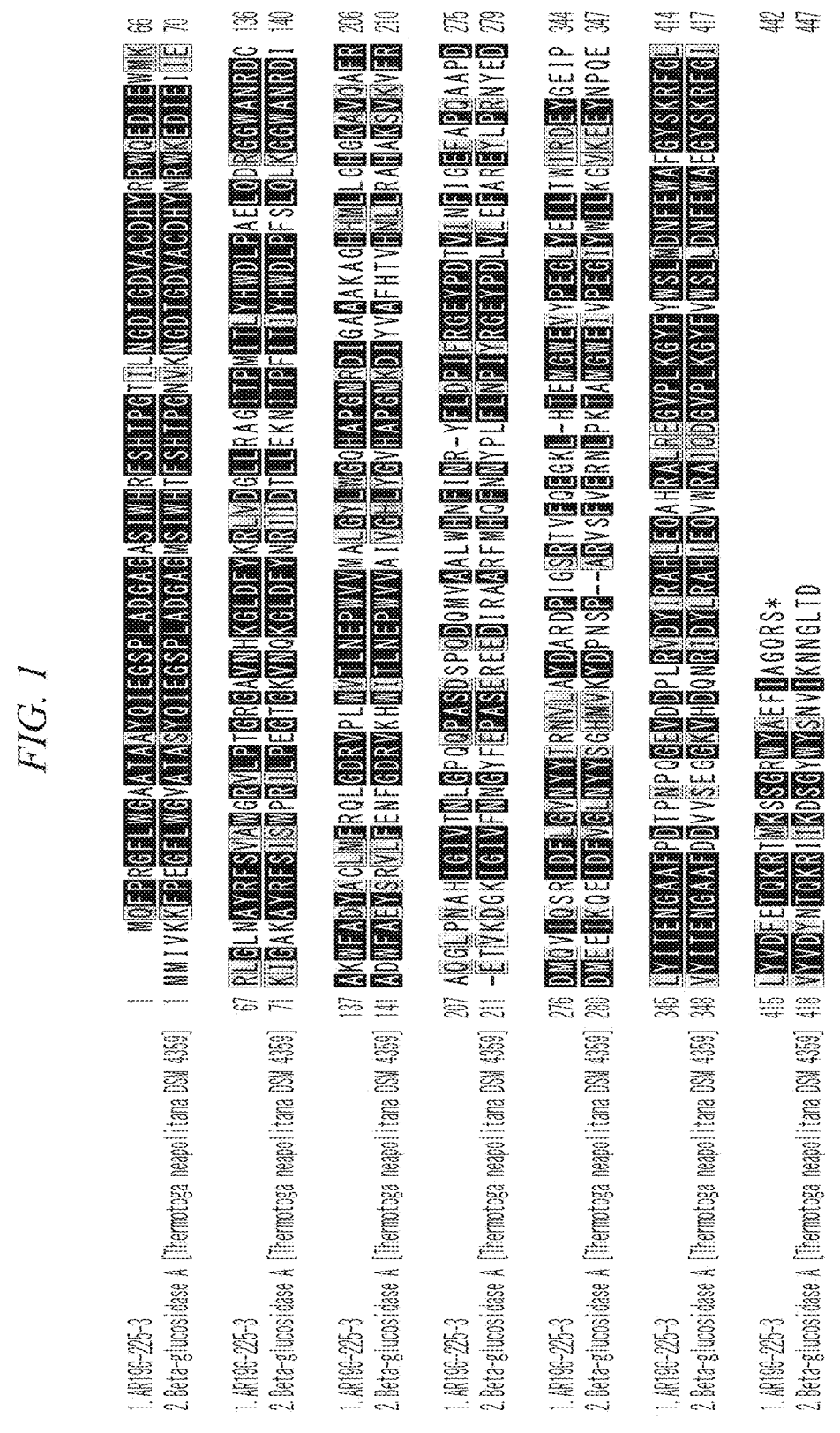

FIG. 1 shows a pairwise alignment of the amino acid sequence of the β-glucosidase catalytic domain of the gene clone AR19G-225-3 and the amino acid sequence of the β-glucosidase A (Genbank registration ID: ACM22958.1) of *Thermotoga neapolitana* DSM 4359. In FIG. 1, the black/white inverted amino acids denote the same amino acid residues (identical) throughout all of these amino acid sequences, the shaded amino acids denote similar amino acid residues (similar) in these amino acid sequences, and the symbols "–" denote deletions (gaps). 251 amino acid residues out of 450 amino acid residues including gaps were identical, such that the β-glucosidase catalytic domain of the open reading frame AR19G-225 showed 55% sequence identity with the β-glucosidase A of *Thermotoga neapolitana* DSM4359.

<6> Gene Cloning

PCR was conducted using a hot spring soil DNA that had been amplified by the genomic DNA amplification kit (GenomiPhi V2 DNA Amplification Kit, manufactured by GE Healthcare) as a template, and by using a forward primer composed of the nucleotide sequence represented by SEQ ID NO: 6 (5'-CACCATGCAGTTTCCACGAGGTTTT-3': obtained by adding 4 nucleotides (CACC) to the 5'-end side of the nucleotide sequence represented by SEQ ID NO: 4. The nucleotides CACC added on the 5' side is a sequence for insertion into a vector) and a reverse primer composed of the nucleotide sequence represented by SEQ ID NO: 5 (5'-TCAACTCCGCTGCCCAGCAAT-3'). It should be noted that the nucleotide sequence represented by SEQ ID NO: 4 is a nucleotide sequence which is homologous (identical) with a partial sequence including the nucleotides at position 1 to 21 of the nucleotide sequence represented by SEQ ID NO: 2 or 3. Moreover, the nucleotide sequence represented by SEQ ID NO: 5 is a nucleotide sequence which is complementary with a partial sequence including the nucleotides at position 1309 to 1329 of the nucleotide sequence represented by SEQ ID NO: 2 or 3. The amplified PCR products were inserted in the pET101/D-TOPO vector of Champion pET Directional TOPO Expression Kits (manufactured by Life Technologies), and transformed into the One Shot TOP10 strain. Positive clones were selected by colony PCR, and then cultured in a LB liquid medium containing 100 mg/L ampicillin at a temperature of 37° C. and 200 rpm for 17 to 20 hours, followed by the preparation of plasmids using the miniprep kit (Wizard plus SV Minipreps DNA Purification System, manufactured by Promega). The prepared plasmids were sequenced by using the 3730 DNA Analyzer (manufactured by Life Technologies Corporation).

One gene clone AR19G-225-3 was obtained from the open reading frame AR19G-225 by PCR cloning. The nucleotide sequence of the β-glucosidase candidate gene AR19G-225-3 included 1,329 by like that of the open reading frame AR19G-225 (SEQ ID NO: 2), and was different from the predicted ORF by one nucleotide. That is, the nucleotide at position 729 was cytosine (C) in the cloned gene (SEQ ID NO: 3), whereas it was thymine (T) in the predicted ORF (SEQ ID NO: 2). However, no difference was observed between the amino acid sequences (SEQ ID NO: 1) to be encoded by them.

The polypeptide (AR19G-225-3) encoded by the β-glucosidase candidate gene AR19G-225-3 (hereinafter, may be referred to as an "AR19G-225-3 gene") was composed of 442 amino acids, and no signal peptide was detected. AR19G-225-3 was a polypeptide in which 441 amino acids (Q2-S442) from glutamine at position 2 to serine at position 442 showed an amino acid sequence of the β-glucosidase catalytic domain belonging to the GH1 family.

<7> Gene Expression and Purification of β-Glucosidase Enzymatic Protein

After the sequencing, the plasmids having the target gene were introduced in *E. coli* for protein expression by a heat shock method. The BL21 Star (DE3) strain furnished in the Champion pET Directional TOPO Expression Kits (manufactured by Life Technologies) was used as the competent cell for the transformation. *E. coli* having the target gene was inoculated in a LB medium containing 100 mg/L ampicillin and cultured to about OD600=0.2 to 0.8, which was then added with IPTG (isopropyl-β-D(−)-thiogalactopyranoside), and additionally cultured for 5 to 20 hours. By so doing, the expression induction of the target protein was carried out. After the culture, *E. coli* was collected by centrifugation, to which 50 mM Tris-HCl buffer (pH8.0) of 1/10-fold volume of the culture liquid was added and suspended. Thereafter, 5 minutes disrupting and 5 minutes halting processes were repeated 7 to 8 times by using an ultrasonic disruption apparatus, Astrason 3000 (manufactured by Misonix, Inc.). By so doing, the crude extract of the gene recombinant *E. coli* containing the target protein was obtained. The crude extract of the gene recombinant *E. coli* was filtrated through a filter (pore diameter φ=0.45 μm, manufactured by Millipore), and the yielded filtrate was used as a gene recombinant *E. coli* homogenate supernatant.

The gene recombinant *E. coli* homogenate supernatant was loaded onto an ion-exchange column HiTrap Q HP (manufactured by GE Healthcare) equilibrated with 50 mM Tris-HCl buffer (pH8.0), by which proteins were fractionated with 0 to 50% concentration gradient with 50 mM Tris-HCl buffer (pH8.0) containing 1M NaCl using a middle-to-high pressure liquid chromatography system AKTA design (manufactured by GE Healthcare). The fractions exhibiting β-glucosidase activity were all mixed and then subjected to solution exchange into 50 mM Tris-HCl buffer (pH8.0) containing 750 mM ammonium sulfate using a centrifugal ultrafiltration membrane VIVASPIN 20 (manufactured by Sartorius stedim). The fractions with β-glucosidase activity after the solution exchange were loaded onto a hydrophobic interaction separation column HiTrap Phenyl HP (manufactured by GE Healthcare) equilibrated with the same solution, by which proteins were fractionated with 0 to 100% concentration gradient with 50 mM Tris-HCl buffer (pH8.0). The fractions exhibiting β-glucosidase activity were all mixed and then concentrated by using the VIVASPIN 20 until the liquid volume reached to about 8 mL. The concentrated sample was added to a gel filtration column Hiload 26/60 superdex 200 pg (manufactured by GE Healthcare) equilibrated with 50 mM Tris-HCl buffer (pH8.0) containing 150 mM NaCl, and fractionated by flowing the same buffer of 1 to 1.5 fold volume of the column volume at a flow rate of 2 to 3 mL/min. The fractions exhibiting β-glucosidase activity were all mixed and then subjected to solution exchange into 50 mM Tris-HCl buffer (pH8.0) and concentrated. By so doing, a purified enzyme having the final concentration of about 1 mg/mL was obtained.

The gene recombinant *E. coli* homogenate supernatant and the purified enzyme were checked by SDS-PAGE (SDS-polyacrylamide gel electrophoresis) analysis. The SDS PAGE of the gene recombinant *E. coli* homogenate supernatant and the purified enzyme were respectively conducted by using the AnykD Criterion TGX Strain-Free Precast Gel (manufactured by Bio-Rad Laboratories, Inc.). The electrophoresis samples prepared by respectively mixing the supernatant or the purified enzyme diluted to 0.13 mg/mL with Tris-SDS βME treatment solution (manufactured by Cosmo Bio Co., Ltd.) at 1:1 were treated at a temperature of 98° C. for 10 minutes. Then, 10 μL of the gene recombinant *E. coli* homogenate supernatant and 10 μL of the purified enzyme per each sample were respectively electrophoresed. After the electrophoresis, the protein bands were visualized by the imaging system ChemiDoc (manufactured by Bio-Rad Laboratories, Inc.).

FIG. 2 shows the SDS-PAGE analysis result of the gene recombinant *E. coli* homogenate supernatant prepared from the transformed *E. coli* introduced with the AR19G-225-3 gene and the purified enzyme which was purified from the gene recombinant *E. coli* homogenate supernatant. The lane 1 is a molecular weight marker for proteins, and the lanes 2 and 3 show the electrophoresis patterns of the gene recombinant *E. coli* homogenate supernatant and the purified enzyme, respectively. As a result, in the gene recombinant *E. coli* homogenate supernatant (lane 2), a strong band was observed near the molecular weight of 50.3 kDa predicted from the amino acid sequence (SEQ ID NO: 1), and in the purified enzyme (lane 3), a single band corresponding with the above band was observed (indicated by an arrow in the figure).

<8> pH and Temperature Dependencies of β-Glucosidase Activity Using PNPG as Substrate PNPG was used as a substrate in the measurement of the β-glucosidase activity. A solution prepared by dissolving PNPG (manufactured by Sigma-Aldrich Co. LLC.) in water and adjusting to a predetermined final concentration was used as a substrate solution. It should be noted that the PNPG aqueous solution prepared by the above method was used as the PNPG substrate solution used for all the following experiments.

The pH dependency of the PNPG hydrolysis activity of the enzymatic protein (AR19G-225-3) encoded by the AR19G-225-3 gene was investigated. In the measurement, a purified enzyme solution prepared by diluting the purified enzyme obtained from the above-mentioned process <7> to 0.08 mg/mL with 50 mM Tris-HCl buffer (pH 8.0) was used.

The measurement of the PNPG hydrolysis activity of the purified enzyme was conducted by allowing a mixture solution composed of 147 μL of a 13.6 mM PNPG aqueous solution, 50 μL of 0.2 M Britton-Robinson buffer (at a pH of 4.0, 5.0, 6.0, 7.0, 7.5, 8.0, 8.5, 9.0, 9.5, or 10.0), 1 μL of purified water, and 2 μL of the purified enzyme solution, to react at a temperature of 70° C. or 85° C. for 15 minutes (substrate final concentration: 10 mM). In all the measurements, a mixture solution prepared by adding 50 mM Tris-HCl buffer (pH8.0) in place of the purified enzyme solution and reacting under the same conditions was used as the control lot. Moreover, the substrate solution and the mixture of the purified enzyme solution and purified water and the buffer were respectively and separately kept at retained reaction temperatures for 5 minutes, and then mixed. This timing was set to the initiation of the reaction. During the reaction, all of the mixed solutions were set to a predetermined temperature by using the Thermomixer (manufactured by Eppendorf AG). After the completion of the reaction, the reaction was stopped by adding the same volume of a 0.2 M Na$_2$CO$_3$ solution to each mixture solution with stirring, followed by centrifugation. By so doing, the supernatant was obtained. The absorbance at 420 nm was measured by using a spectrophotometer, and the amount of p-nitrophenol in the supernatant was calculated by using a calibration curve prepared with p-nitrophenol, and the amount of p-nitrophenol produced by the enzymatic hydrolysis was obtained by the difference from the control lot. The enzymatic activity for producing 1 μmol of p-nitrophenol per minute was defined as 1 U, and the value obtained by dividing it by the amount of protein was defined as the specific activity (U/mg). In addition, each measurement was performed by three independent experiments, from which the mean value and the standard errors were obtained.

Then, the temperature dependency of the PNPG hydrolysis activity of the purified AR19G-225-3 was investigated.

The measurement of the PNPG hydrolysis activity of the purified enzyme was conducted by performing the enzymatic reaction in the same manner as in the case of examining the pH dependency of the PNPG hydrolysis activity of AR19G-225-3, except for using a 0.2 M phosphoric acid buffer of a pH of 7.5 or 8.0 in place of the Britton-Robinson buffer and conducting at a reaction temperature of 50, 60, 70, 75, 80, 85, 90, 95, or 99° C. Then, the absorbance at 420 nm of the supernatant of the mixture solution after the reaction was measured to obtain the amount of p-nitrophenol produced by the hydrolysis.

Figure 3:
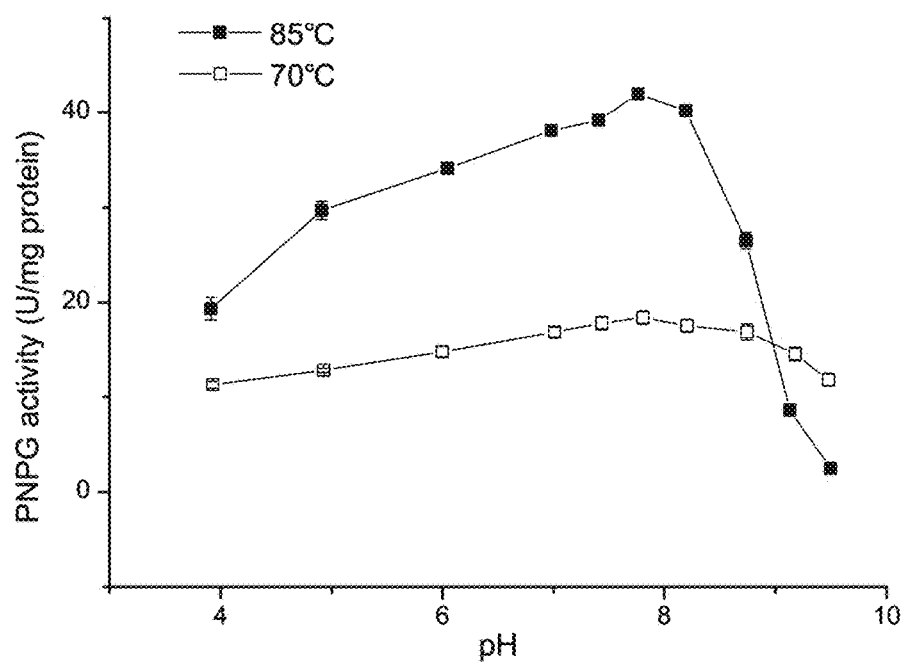
FIG. 3 is a diagram showing the results of the PNPG hydrolysis activity (at 70° C. or 85° C.) of the AR19G-225-3 protein expressed in *E. coli* measured at respective pH values in Example 1.
Figure 4:
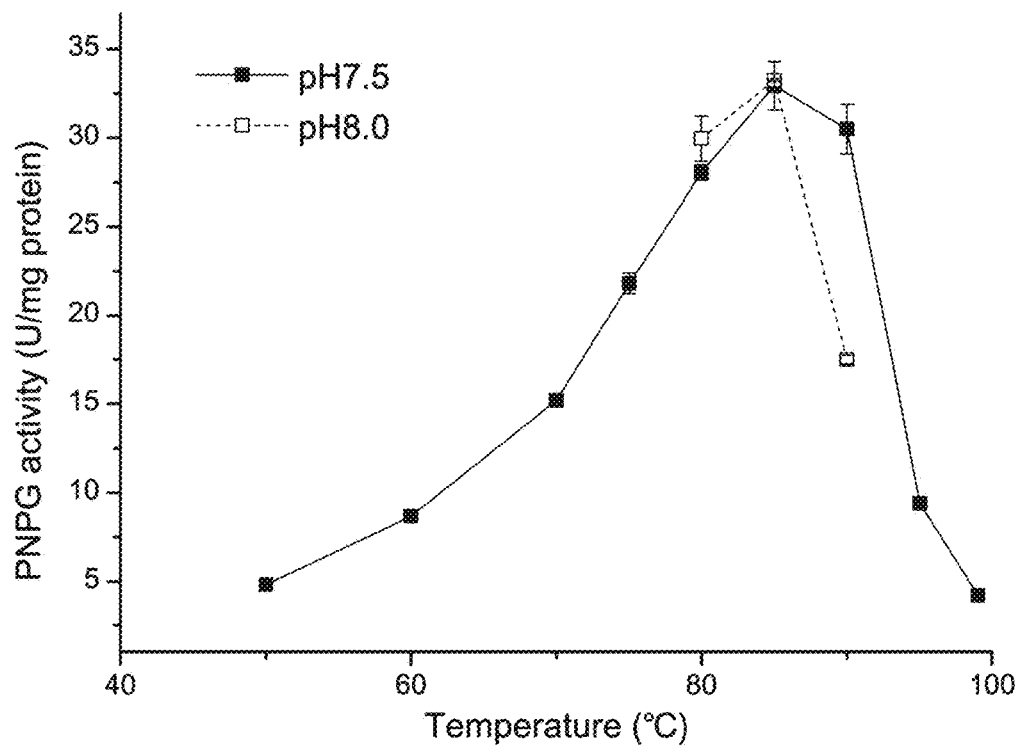
FIG. 4 is a diagram showing the results of the PNPG hydrolysis activity (at a pH of 7.5 or a pH of 8.0) of the AR19G-225-3 protein expressed in *E. coli* measured at respective temperatures in Example 1.

The measurement results are shown in FIGS. 3 and 4. FIG. 3 is a diagram showing the measurement results of the PNPG hydrolysis activity of the purified enzyme AR19G-225-3 at a temperature of 70° C. or 85° C. at respective pH values, wherein the horizontal axis represents the pH. FIG. 4 is a diagram showing the measurement results of the PNPG hydrolysis activity (pH7.5 or pH8.0) at respective temperatures, wherein the horizontal axis represents the temperature. The pH was plotted by the actual measurement values of the mixture solution containing the substrate, the buffer, and the enzyme.

The purified enzyme of AR19G-225-3 exhibited high PNPG hydrolysis activity in a temperature range from 75 to 90° C. (FIG. 4). The optimum temperature ($T_{opt}$) showing the highest activity was 85° C. at a pH of 7.5 and 8.0. When the enzymatic reaction temperature was set to 95° C. or higher, the PNPG hydrolysis activity of the purified enzyme of AR19G-225-3 was rapidly decreased.

The purified enzyme of AR19G-225-3 exhibited high PNPG hydrolysis activity within a range of pH5 to 9 at a reaction temperature from 70 to 85° C. (FIG. 3). The optimum pH varied depending on the reaction temperature, which was a pH of 7.81 (actual measurement value) at a temperature of 70° C., and a pH of 7.77 (actual measurement value) at a temperature of 85° C. A low level of PNPG hydrolysis activity was observed in the purified enzyme of AR19G-225-3 in a pH range of 9.13 to 9.50 at a reaction temperature of 85° C.

<9> Substrate Specificity of AR19G-225-3

The hydrolysis activities for various cellulose substrates and hemicellulose substrates were investigated with the enzymatic protein (AR19G-225-3) encoded by the AR19G-225-3 gene. In the measurement, a purified enzyme solution prepared by diluting the purified enzyme obtained from the above-mentioned process <7> to 0.08 mg/mL with 50 mM Tris-HCl buffer (pH 8.0) was used. In addition, as substrates, PNPG (manufactured by Sigma-Aldrich Co. LLC.), PNPX (manufactured by Sigma-Aldrich Co. LLC.), CMC (manufactured by Sigma-Aldrich Co. LLC.), PSA, and xylan (derived from beechwood, manufactured by Sigma-Aldrich Co. LLC.) were used.

PSA was prepared by once dissolving an Avicel powder (fine crystalline cellulose powder, manufactured by Merck) with a phosphoric acid solution, then precipitating it by adding sterile purified water, and thereafter washing the same until the pH reached 5 or higher. It should be noted that PSA used for all the following experiments was prepared by the above method.

More specifically, as a reaction solution, a mixture solution composed of 50 μL of phosphoric acid buffer at a pH of 8.0, 2 μL of the purified enzyme solution, the substrate aqueous solution and purified water was used. The concentration and amount of the substrate solution and the amount of purified water to be added to the mixture solution were set in such a manner that 147 μL of a 13.6 mM substrate aqueous solution and 1 μL of purified water were added when PNPG or PNPX was used as the substrate, 100 μL of a 1% by mass substrate aqueous solution and 48 μL of purified water were added when CMC, PSA or xylan was used as the substrate.

Each mixture solution was incubated at a temperature of 70° C. or 85° C. for 15 minutes to thereby carry out the enzymatic reaction. The substrate solution and the mixture of the purified enzyme solution and purified water and the buffer were respectively and separately kept at retained reaction temperatures for 5 minutes, and then mixed. This timing was set to the initiation of the reaction. In addition, when PSA, and xylan were used as substrates, during the reaction, agitation at 1,400 rpm was applied to the mixture solution using the Thermomixer (manufactured by Eppendorf AG) so as to avoid the precipitation of the substrate.

In the reaction where PNPG or PNPX was used as the substrate, after the completion of the reaction, as in the case of investigating the pH dependency of the PNPG hydrolysis activity of AR19G-225-3 of the above-mentioned process <8>, the absorbance at 420 nm of the supernatant of the mixture solution after the reaction was measured to obtain the amount of p-nitrophenol produced by the hydrolysis. In the reaction where CMC, PSA, or xylan was used as a substrate, after the completion of the reaction, the same volume of a 3,5-dinitrosalicylic acid reagent (DNS solution) was added. The resulting mixture was treated by heating at a temperature of 100° C. for 5 minutes, cooled down on ice for 5 minutes, and then centrifuged at 17,400 g for 5 minutes at room temperature. By so doing, the supernatant was obtained. The absorbance at 540 nm was measured by using a spectrophotometer, and the amount of reduced sugar in the supernatant was calculated by using a calibration curve prepared with glucose (calibration curve prepared with xylose when xylan was used as a substrate). The amount of reduced sugar produced by the enzymatic hydrolysis was obtained by the difference from the control lot. The enzymatic activity for producing 1 μmol of reduced sugar per minute was defined as 1 U, and the value obtained by dividing it by the amount of protein was defined as the specific activity (U/mg).

Figure 5:
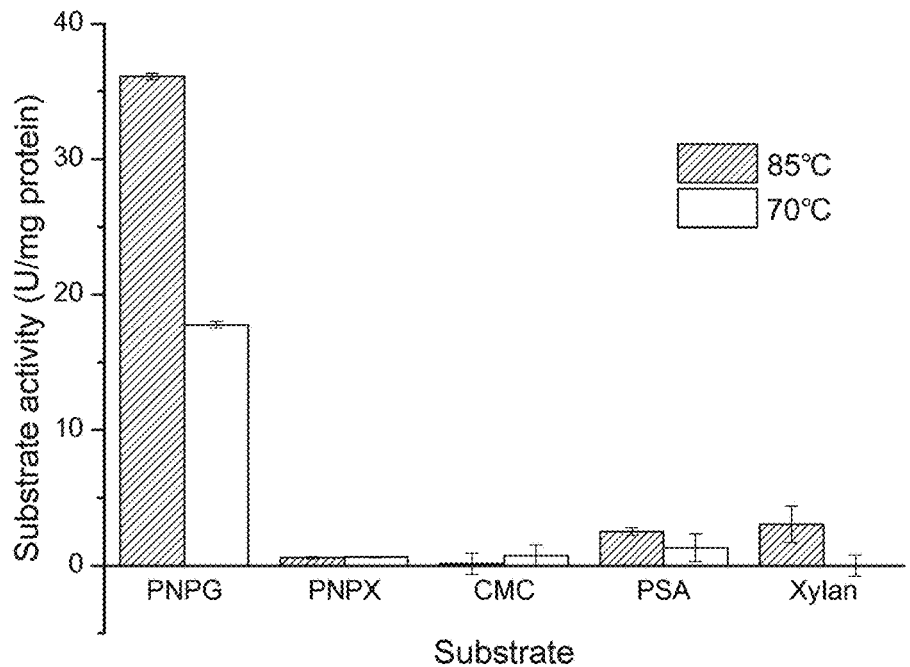
FIG. 5 is a diagram showing the measurement results of the β-glucosidase activity of the AR19G-225-3 protein expressed in *E. coli* in Example 1 for each substrate.

Each measurement was performed by three independent experiments, from which the mean value and the standard errors were obtained. The measurement results are shown in FIG. 5.

As a result, AR19G-225-3 exhibited high hydrolysis activity for PNPG, and also exhibited a certain level of degradation activity for PSA and xylan (particularly at 85° C.). From these results, it was shown that AR19G-225-3 was β-glucosidase and also had a certain level of xylanase activity.

<10> Thermal Stability Measurement of β-Glucosidase by Differential Scanning Fluorimetry Differential scanning fluorimetry (DSF) is one of the methods of measuring the thermal denaturation of proteins using a fluorescent dye and a real-time PCR machine, and can be applied to various proteins. The fluorescent dyes used in DSF such as SYPRO Orange emit fluorescence in the nonpolar conditions when binding to the hydrophobic site, while the emission is suppressed in the polar conditions when dissolved in water. Usually, the protein structure is unfolded in the thermal denaturation temperature, and the hydrophobic regions of the protein are exposed to the protein surface. When SYPRO Orange binds to this exposed hydrophobic region, by the excitation light having a wavelength of 470 to 480 nm, strong fluorescence having a peak near a wavelength of 595 nm is emitted. By increasing the temperature of the protein solution at regular intervals in a stepwise manner and measuring the fluorescence intensity, the thermal degradation temperature (=change point of the fluorescence intensity) is calculated.

In the measurement, a purified enzyme solution prepared by adjusting the purified enzyme obtained from the above-mentioned process <7> to 1 mg/mL was used.

More specifically, 2 μL of 100-fold diluted SYPRO Orange (manufactured by Life Technologies), 1 μL of the purified enzyme solution with a concentration of 1 mg/mL, 5 μL of 200 mM phosphoric acid buffer (pH 8.0) and 12 μL of purified water were added into the wells of a 96-well PCR plate (Multiplate 96 Well PCR Plate MLL-9651, manufactured by Bio-Rad Laboratories, Inc.) so that the volume of each well was 20 μL. The PCR plate was sealed with Optical Flat 8-Cap Strips (manufactured by Bio-Rad Laboratories, Inc.), the temperature of the well was increased by 0.2° C. from 30° C. up to 100° C. by a real-time PCR machine (CFX96 Touch Real-Time PCR System, manufactured by Bio-Rad Laboratories, Inc.), and following a lapse of 10 seconds after the target temperature was achieved, the fluorescence intensity of each well was measured simultaneously. SYPRO Orange was excited by a light emitting diode (LED) having a wavelength range of 450 to 490 nm, the SYPRO Orange emitted light was passed through a band pass filter of 560 to 580 nm range, the measurement of the fluorescence intensity was performed with a CCD camera, and changes in the fluorescence intensity were plotted as a function of temperature. The data analysis was carried out using the analysis software CFX Manager (manufactured by Bio-Rad Laboratories, Inc.) supplied with the real-time PCR machine. Each measurement was performed by three independent experiments.

Figure 6:
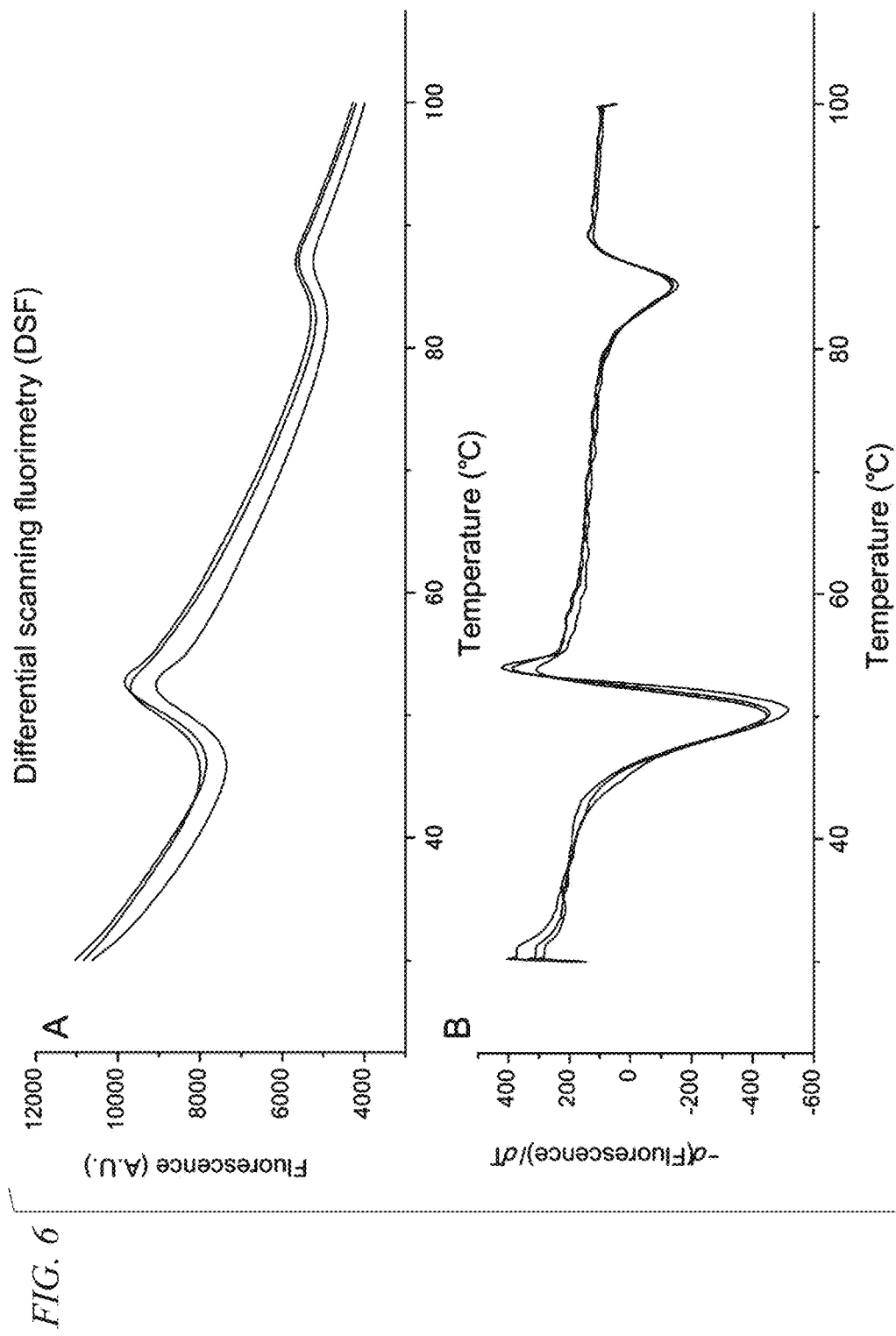
FIG. 6 is a diagram showing a change in the fluorescence intensity of SYPRO Orange caused in association with the thermal denaturation exhibited by the AR19G-225-3 protein expressed in *E. coli* in Example 1.

FIG. 6 shows changes in the fluorescence intensity of SYPRO Orange caused in association with the thermal denaturation exhibited by the AR19G-225-3 enzymatic protein which was measured by the DSF method. The upper graph in FIG. 6 shows measured data, and the lower graph in FIG. 6 shows the first derivative "−d(Fluorescence)/dt" of the fluorescence intensity change curve in the upper graph of FIG. 6. The thermal denaturation temperature (melting temperature; Tm value) was defined as the local minimum value of the first derivative ("−d(Fluorescence)/dt" shown on the Y axis of the lower graph in FIG. 6) of the fluorescence intensity curve that is a function of temperature.

In the first derivative of the fluorescence intensity curve of AR19G-225-3, the local minimum points were observed at two locations near 50° C. and 85° C. Since the AR19G-225-3 enzymatic protein also exhibited the enzymatic activity over 60° C., it was thought that the local minimum point near 50° C. suggested some sort of structural change in the protein molecule but did not indicate the thermal denaturation, and the actual thermal denaturation temperature was indicated by the local minimum point of around 85° C. The average Tm value of the AR19G-225-3 enzyme protein was 85.2° C., which was close to the optimum temperature $T_{opt}$=85° C. of the enzyme determined from the β-glucosidase activity.

[Sequence Listing]

```
                        SEQUENCE LISTING

<160> NUMBER OF SEQ ID NOS: 7

<210> SEQ ID NO 1
<211> LENGTH: 442
<212> TYPE: PRT
<213> ORGANISM: Unknown
<220> FEATURE:
<223> OTHER INFORMATION: Amino acid sequence of AR19G-225-3; present in
      natural; obtained from microbial groups collected form high
      temperature hot spring soils

<400> SEQUENCE: 1

Met Gln Phe Pro Arg Gly Phe Leu Trp Gly Ala Ala Thr Ala Ala Tyr
1               5                   10                  15

Gln Ile Glu Gly Ser Pro Leu Ala Asp Gly Ala Gly Ala Ser Ile Trp
            20                  25                  30

His Arg Phe Ser His Thr Pro Gly Thr Ile Leu Asn Gly Asp Thr Gly
        35                  40                  45

Asp Val Ala Cys Asp His Tyr Arg Arg Trp Gln Glu Asp Ile Glu Trp
    50                  55                  60

Met Lys Arg Leu Gly Leu Asn Ala Tyr Arg Phe Ser Val Ala Trp Gly
65                  70                  75                  80

Arg Val Leu Pro Thr Gly Arg Gly Ala Val Asn His Lys Gly Leu Asp
                85                  90                  95

Phe Tyr Lys Arg Leu Val Asp Gly Leu Leu Arg Ala Gly Ile Thr Pro
            100                 105                 110

Met Ile Thr Leu Tyr His Trp Asp Leu Pro Ala Glu Leu Gln Asp Arg
        115                 120                 125

Gly Gly Trp Ala Asn Arg Asp Cys Ala Lys Trp Phe Ala Asp Tyr Ala
    130                 135                 140

Cys Leu Met Phe Arg Gln Leu Gly Asp Arg Val Pro Leu Trp Val Thr
145                 150                 155                 160

Leu Asn Glu Pro Trp Val Val Met Ala Leu Gly Tyr Leu Trp Gly Gln
                165                 170                 175

His Ala Pro Gly Met Arg Asp Ile Gly Ala Ala Ala Lys Ala Gly His
            180                 185                 190

His Met Leu Leu Gly His Gly Lys Ala Val Gln Ala Phe Arg Ala Gln
        195                 200                 205

Gly Leu Pro Asn Ala His Ile Gly Ile Val Thr Asn Leu Gly Pro Gln
    210                 215                 220

Gln Pro Ala Ser Asp Ser Pro Gln Asp Gln Met Val Ala Ala Leu Trp
225                 230                 235                 240

His Asn Phe Ile Asn Arg Tyr Phe Leu Asp Pro Ile Phe Arg Gly Glu
                245                 250                 255

Tyr Pro Asp Thr Val Ile Asn Phe Ile Gly Glu Phe Ala Pro Gln Ala
            260                 265                 270

Ala Pro Asp Asp Met Gln Val Ile Gln Ser Arg Ile Asp Phe Leu Gly
        275                 280                 285

Val Asn Tyr Tyr Thr Arg Asn Val Leu Ala Tyr Asp Ala Arg Asp Pro
    290                 295                 300
```

```
Ile Gly Ser Arg Thr Val Phe Gln Glu Gly Lys Leu His Thr Glu Met
305                 310                 315                 320

Gly Trp Glu Val Tyr Pro Glu Gly Leu Tyr Glu Ile Leu Thr Trp Ile
                325                 330                 335

Arg Asp Glu Tyr Gly Glu Ile Pro Leu Tyr Ile Thr Glu Asn Gly Ala
                340                 345                 350

Ala Phe Pro Asp Thr Pro Asn Pro Gln Gly Glu Val Asp Asp Pro Leu
                355                 360                 365

Arg Val Asp Tyr Ile Arg Ala His Leu Glu Gln Ala His Arg Ala Leu
                370                 375                 380

Arg Glu Gly Val Pro Leu Lys Gly Tyr Phe Tyr Trp Ser Leu Met Asp
385                 390                 395                 400

Asn Phe Glu Trp Ala Phe Gly Tyr Ser Lys Arg Phe Gly Leu Leu Tyr
                405                 410                 415

Val Asp Phe Glu Thr Gln Lys Arg Thr Met Lys Ser Ser Gly Arg Trp
                420                 425                 430

Tyr Ala Glu Phe Ile Ala Gly Gln Arg Ser
                435                 440
```

<210> SEQ ID NO 2
<211> LENGTH: 1329
<212> TYPE: DNA
<213> ORGANISM: Unknown
<220> FEATURE:
<223> OTHER INFORMATION: Open reading frame AR19G-225 encoded a
      polypeptide of SEQ ID NO: 1; present in natural; obtained from
      microbial groups collected form high temperature hot spring soils

<400> SEQUENCE: 2

```
atgcagtttc cacgaggttt tctctggggc gcggcgaccg cggcgtatca gatcgaaggc      60
tcgcccttag ccgatggggc gggtgcgtcc atctggcacc gatttagcca tacgccagga     120
acgattctca acggcgacac gggcgatgtg cgtgcgatc actatcgccg ctggcaggaa      180
gacatcgagt ggatgaaacg gttaggcttg aacgccatc gcttttcggt ggcgtggggg      240
cgtgtgcttc cgacgggacg gggcgcggtc aatcacaaag gactggattt ctataaacgc     300
ctcgtggacg gtctgctacg agcgggcatt acgcccatga ttaccctcta ccactgggac     360
ctgcctgcgg aacttcagga ccgtggcggt tgggcgaacc gcgactgcgc aaaatggttt     420
gcagactatg catgtttgat gtttcgccag cttggcgatc gagtcccgct ttgggtgacg     480
ctgaacgagc cgtgggtggt catggcgctg gctatctttt ggggcagca tgcgcccggc     540 atgcgtgaca tcgcgccgc ggcgaaagcg ggacatcata tgctcttagg cacggcaaa      600 gcggtgcagg cgtttcgcgc acaaggactg cctaacgccc acatcggcat cgtgacgaac     660
ctcggtcccc aacagcccgc cagcgatagc cctcaagacc agatggtcgc cgcgttatgg     720
cacaacttta tcaatcgcta cttttagac cctatcttcc gcggcgagta ccccgacaca     780
gtgattaatt tcatcggcga gtttgcgccc aagcggcgc ctgacgatat gcaggttat     840 caaagccgaa ttgactttct gggcgtaaac tattacacgc gcaatgtgct tgcttacgat     900
gcgcgcgacc ctatcggttc gcggacggtg ttccaagagg gcaaactaca caccgaaatg     960
gggtgggagg tctatccaga aggcttgtac gaaatcctca catggattcg cgacgagtat    1020
ggcgagattc cgctctacat caccgagaac ggcgcggcgt tccccgacac gcctaacccg    1080
caaggcgagg tggacgaccc ccttcgggtg gactacattc gcgcgcactt ggagcaggcg    1140
catcgcgccc tccgagaggg cgtcccgctc aaagggtatt tctactggtc gctaatggac    1200
```

```
aacttcgagt gggcatttgg ctacagcaag cggtttgggt tgctctatgt tgattttgag    1260
acccagaagc gcacgatgaa gtccagcggt cgctggtacg ctgagttcat tgctgggcag    1320
cggagttga                                                            1329
```

<210> SEQ ID NO 3
<211> LENGTH: 1329
<212> TYPE: DNA
<213> ORGANISM: Unknown
<220> FEATURE:
<223> OTHER INFORMATION: Nucleotide sequence of AR19G-225-3; present in
      natural; obtained from microbial groups collected form high
      temperature hot spring soils

<400> SEQUENCE: 3

```
atgcagtttc cacgaggttt tctctggggc gcggcgaccg cggcgtatca gatcgaaggc      60
tcgcccttag ccgatggggc gggtgcgtcc atctggcacc gatttagcca tacgccagga    120
acgattctca acggcgacac gggcgatgtg gcgtgcgatc actatcgccg ctggcaggaa    180
gacatcgagt ggatgaaacg gttaggcttg aacgccatcg cttttcggt ggcgtggggg     240 cgtgtgcttc cgacgggacg gggcgcggtc aatcacaaag gactggattt ctataaacgc    300
ctcgtggacg gtctgctacg agcgggcatt acgcccatga ttaccctcta ccactgggac    360
ctgcctgcgg aacttcagga ccgtggcggt tgggcgaacc gcgactgcgc aaaatggttt    420
gcagactatg catgtttgat gtttcgccag cttggcgatc gagtcccgct ttgggtgacg    480
ctgaacgagc cgtgggtggt catggcgctg ggctatcttt ggggcagca tgcgcccggc    540 atgcgtgaca tcgcgccgc ggcgaaagcg ggacatcata tgctcttagg gcacggcaaa    600
gcggtgcagg cgtttcgcgc acaaggactg cctaacgccc acatcggcat cgtgacgaac    660
ctcggtcccc aacagcccgc cagcgatagc cctcaagacc agatggtcgc cgcgttatgg    720
cacaacttca tcaatcgcta cttttagac cctatcttcc gcggcgagta ccccgacaca    780
gtgattaatt tcatcggcga gtttgcgccc caagcggcgc ctgacgatat gcaggttatt    840
caaagccgaa ttgactttct gggcgtaaac tattacacgc gcaatgtgct tgcttacgat    900
gcgcgcgacc ctatcggttc gcggacggtg ttccaagagg gcaaactaca caccgaaatg    960
gggtgggagg tctatccaga aggcttgtac gaaatcctca catggattcg cgacgagtat   1020
ggcgagattc cgctctacat caccgagaac ggcgcggcgt tccccgacac gcctaacccg   1080
caaggcgagg tggacgaccc ccttcgggtg gactacattc gcgcgcactt ggagcaggcg   1140
catcgcgccc tccgagaggg cgtcccgctc aaagggtatt tctactggtc gctaatggac   1200
aacttcgagt gggcatttgg ctacagcaag cggtttgggt tgctctatgt tgattttgag   1260
acccagaagc gcacgatgaa gtccagcggt cgctggtacg ctgagttcat tgctgggcag   1320
cggagttga                                                          1329
```

<210> SEQ ID NO 4
<211> LENGTH: 21
<212> TYPE: DNA
<213> ORGANISM: Artificial Sequence
<220> FEATURE:
<223> OTHER INFORMATION: Nucleotide sequence which is homologous with a
      partial sequence including the nucleotides at position 1 to 21 of
      the nucleotide sequence of SEQ ID NO: 2 or 3; partial sequence for
      design of primers of SEQ ID NO: 5 and 6; artificially synthesized

<400> SEQUENCE: 4

```
atgcagtttc cacgaggttt t                                               21
```

-continued

<210> SEQ ID NO 5
<211> LENGTH: 21
<212> TYPE: DNA
<213> ORGANISM: Artificial Sequence
<220> FEATURE:
<223> OTHER INFORMATION: Reverse primer having a nucleotide sequence
      which is complementary with a partial sequence including the
      nucleotides at position 1309 to 1329 of the nucleotide sequence of
      SEQ ID NO: 2 or 3; primer for gene cloning; artificially
      synthesized

<400> SEQUENCE: 5
tcaactccgc tgcccagcaa t                                            21

<210> SEQ ID NO 6
<211> LENGTH: 25
<212> TYPE: DNA
<213> ORGANISM: Artificial Sequence
<220> FEATURE:
<223> OTHER INFORMATION: Forward primer in which 4 nucleotides (CACC)
      were added to the 5'-end side of the nucleotide sequence of SEQ ID
      NO: 4 ; primer for gene cloning; artificially synthesized

<400> SEQUENCE: 6
caccatgcag tttccacgag gtttt                                        25

<210> SEQ ID NO 7
<211> LENGTH: 447
<212> TYPE: PRT
<213> ORGANISM: Unknown
<220> FEATURE:
<223> OTHER INFORMATION: Amino acid sequence of a beta-glucosidase A of
      Thermotoga neapolitana DSM 4359; has a homology with an amino acid
      sequence of a beta-glucosidase A of Thermotoga neapolitana DSM
      4359, and this homology (sequence identity) is 55%; present in
      natural

<400> SEQUENCE: 7

Met Met Ile Val Lys Lys Phe Pro Glu Gly Phe Leu Trp Gly Val Ala
1               5                   10                  15

Thr Ala Ser Tyr Gln Ile Glu Gly Ser Pro Leu Ala Asp Gly Ala Gly
            20                  25                  30

Met Ser Ile Trp His Thr Phe Ser His Thr Pro Gly Asn Val Lys Asn
        35                  40                  45

Gly Asp Thr Gly Asp Val Ala Cys Asp His Tyr Asn Arg Trp Lys Glu
    50                  55                  60

Asp Ile Glu Ile Ile Glu Lys Ile Gly Ala Lys Ala Tyr Arg Phe Ser
65                  70                  75                  80

Ile Ser Trp Pro Arg Ile Leu Pro Glu Gly Thr Gly Lys Val Asn Gln
                85                  90                  95

Lys Gly Leu Asp Phe Tyr Asn Arg Ile Ile Asp Thr Leu Leu Glu Lys
            100                 105                 110

Asn Ile Thr Pro Phe Ile Thr Ile Tyr His Trp Asp Leu Pro Phe Ser
        115                 120                 125

Leu Gln Leu Lys Gly Gly Trp Ala Asn Arg Asp Ile Ala Asp Trp Phe
    130                 135                 140

Ala Glu Tyr Ser Arg Val Leu Phe Glu Asn Phe Gly Asp Arg Val Lys
145                 150                 155                 160

His Trp Ile Thr Leu Asn Glu Pro Trp Val Val Ala Ile Val Gly His
                165                 170                 175

Leu Tyr Gly Val His Ala Pro Gly Met Lys Asp Ile Tyr Val Ala Phe
            180                 185                 190

-continued

```
His Thr Val His Asn Leu Leu Arg Ala His Ala Lys Ser Val Lys Val
        195                 200                 205
Phe Arg Glu Thr Val Lys Asp Gly Lys Ile Gly Ile Val Phe Asn Asn
    210                 215                 220
Gly Tyr Phe Glu Pro Ala Ser Glu Arg Glu Glu Asp Ile Arg Ala Ala
225                 230                 235                 240
Arg Phe Met His Gln Phe Asn Asn Tyr Pro Leu Phe Leu Asn Pro Ile
            245                 250                 255
Tyr Arg Gly Glu Tyr Pro Asp Leu Val Leu Glu Phe Ala Arg Glu Tyr
            260                 265                 270
Leu Pro Arg Asn Tyr Glu Asp Asp Met Glu Glu Ile Lys Gln Glu Ile
            275                 280                 285
Asp Phe Val Gly Leu Asn Tyr Tyr Ser Gly His Met Val Lys Tyr Asp
    290                 295                 300
Pro Asn Ser Pro Ala Arg Val Ser Phe Val Glu Arg Asn Leu Pro Lys
305                 310                 315                 320
Thr Ala Met Gly Trp Glu Ile Val Pro Glu Gly Ile Tyr Trp Ile Leu
            325                 330                 335
Lys Gly Val Lys Glu Glu Tyr Asn Pro Gln Glu Val Tyr Ile Thr Glu
            340                 345                 350
Asn Gly Ala Ala Phe Asp Asp Val Val Ser Glu Gly Gly Lys Val His
            355                 360                 365
Asp Gln Asn Arg Ile Asp Tyr Leu Arg Ala His Ile Glu Gln Val Trp
    370                 375                 380
Arg Ala Ile Gln Asp Gly Val Pro Leu Lys Gly Tyr Phe Val Trp Ser
385                 390                 395                 400
Leu Leu Asp Asn Phe Glu Trp Ala Glu Gly Tyr Ser Lys Arg Phe Gly
            405                 410                 415
Ile Val Tyr Val Asp Tyr Asn Thr Gln Lys Arg Ile Ile Lys Asp Ser
            420                 425                 430
Gly Tyr Trp Tyr Ser Asn Val Ile Lys Asn Asn Gly Leu Thr Asp
            435                 440                 445
```

What is claimed is:

1. An isolated polypeptide comprising a protein having β-glucosidase activity and an amino acid sequence that is heterologous to the protein having β-glucosidase activity, wherein the amino acid sequence of the protein having β-glucosidase activity comprises the amino acid sequence of SEQ ID NO: 1 and wherein the heterologous amino acid sequence is selected from the group consisting of a cellulose-binding module, a linker domain, a signal peptide and a purification tag.

2. The polypeptide according to claim 1, which also has axylanase activity.

3. A glycoside hydrolase mixture, comprising the polypeptide according to claim 1 and at least one additional glycoside hydrolase.

4. A method for producing a lignocellulose degradation product, the method comprising contacting a material comprising lignocellulose with the polypeptide according to claim 1, to thereby produce a lignocellulose degradation product.

5. A method for producing a lignocellulose degradation product, the method comprising contacting a material comprising lignocellulose with the glycoside hydrolase mixture according to claim 3, to thereby produce a lignocellulose degradation product.

* * * * *